United States Patent [19]

Nesvadba et al.

[11] Patent Number: 5,607,624
[45] Date of Patent: Mar. 4, 1997

[54] PROCESS FOR THE PREPARATION OF 3-ARYLBENZOFURANONES

[75] Inventors: Peter Nesvadba; Samuel Evans, both of Marly, Switzerland; Ralf Schmitt, Bensheim, Germany

[73] Assignee: Ciba-Geigy Corporation, Tarrytown, N.Y.

[21] Appl. No.: 304,455

[22] Filed: Sep. 12, 1994

[30] Foreign Application Priority Data

Sep. 17, 1993 [CH] Switzerland .............. 2812/93

[51] Int. Cl.⁶ .............. F21V 9/04; C07D 305/12
[52] U.S. Cl. .............. 252/589; 544/238; 544/239; 544/240; 544/242; 544/283; 544/285; 544/286; 544/287; 544/288; 544/333; 544/347; 546/138; 546/139; 546/141; 546/142; 546/147; 546/148; 546/152; 546/153; 546/155; 546/156; 546/157; 548/525; 549/13; 549/23; 549/26; 549/27; 549/43; 549/44; 549/45; 549/46; 549/48; 549/49; 549/51; 549/52; 549/55; 549/58; 549/60; 549/307
[58] Field of Search .............. 252/582, 589; 549/307, 13, 23, 26, 27, 43, 44, 45, 46, 48, 49, 51, 52, 55, 58, 60; 544/238, 239, 240, 242, 283, 285, 286, 287, 288, 333, 347; 546/138, 139, 141, 142, 147, 148, 152, 153, 155, 156, 157; 548/525

[56] References Cited

U.S. PATENT DOCUMENTS

| | | | |
|---|---|---|---|
| 4,013,690 | 3/1977 | Closse et al. | 549/307 |
| 4,325,863 | 4/1982 | Hinsken et al. | 624/111 |
| 4,338,244 | 7/1982 | Hinsken et al. | 118/11 |
| 5,175,312 | 12/1992 | Dubs et al. | 549/307 |
| 5,428,177 | 6/1995 | Nesvadba | 549/307 |

FOREIGN PATENT DOCUMENTS

| | | |
|---|---|---|
| 2106608 | 3/1994 | Canada . |
| 0589839 | 3/1994 | European Pat. Off. . |

OTHER PUBLICATIONS

J. Org. Chem. 1992, 57, pp. 362–366.
Applied Catalysis, 61 (1990), pp. 1–25.
J. C. S. Chem. Comm., 1980, pp. 851–852.
J. Chem. Soc., Chem. Commun., 1989 pp. 1353–1354.
Monatshefte für Chemie 99, pp. 990–994 (1968).
Monatshefte für Chemie 99, pp. 2223–2226 (1968).
Beilstein, E. III/IV 18 pp. 154–166 (1975).
Beilstein 18, 17 (1934).
J. Morvan et al., Bull. Soc. Chim. FR. 1979, 583–591.
M. Julia, et al., Bull. Soc. Chim. FR. 1965, 2175–2182.
Houben–Weyl, vol. VI/IC, p. 1030 (1976).
Organikum, pp. 186–191 (1986).
Organikum, pp. 402–408 (1986).

*Primary Examiner*—Philip Tucker
*Attorney, Agent, or Firm*—Michele A. Kovaleski; Luther A. R. Hall

[57] ABSTRACT

A process for the preparation of compounds of formula I

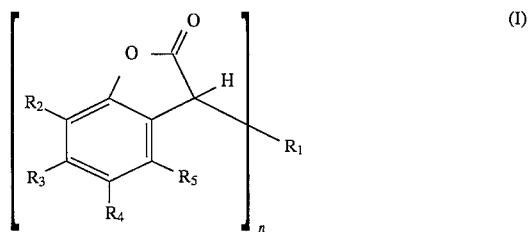

wherein the general symbols are as defined in claim 1, which comprises reacting a compound of formula III

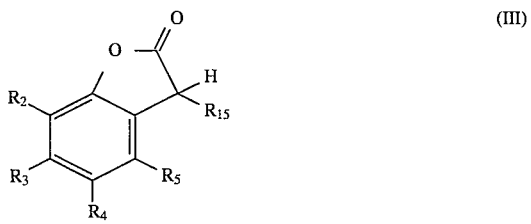

wherein the general symbols are as defined in claim 1, with a compound of formula IV

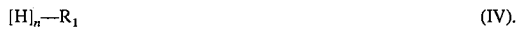

21 Claims, No Drawings

PROCESS FOR THE PREPARATION OF 3-ARYLBENZOFURANONES

The present invention relates to a novel process for the preparation of 3-arylbenzofuranones that are suitable for stabilising organic materials against oxidative, thermal or light-induced degradation.

Individual benzofuran-2-ones are known in the literature, and have been mentioned, inter alia, in Beilstein 18, 17 and Beilstein E III/IV, 18, 154–166, or described by Th. Kappe et al., Monatshefte für Chemie 99, 990 (1968); J. Morvan et al., Bull. Soc. Chim. Fr. 1979, 583; L. F. Clarke et al., J. Org. Chem. 57, 362 (1992); M. Julia et al., Bull. Soc. Chim. Fr. 1965, 2175, or by H. Sterk et al., Monatshefte für Chemie 99, 2223 (1968). In no publication are these compounds used as stabilisers for organic materials.

The use of some 3-phenyl-3H-benzofuran-2-ones as stabilisers for organic polymers is disclosed, inter alia, in U.S. Pat. Nos. 4,325,863; 4,338,244 and 5,175,312.

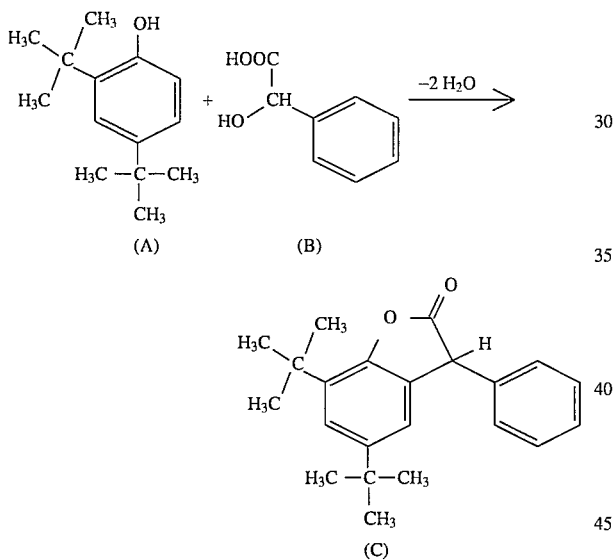

The hitherto preferred process for the preparation of 3-phenyl-3H-benzofuran-2-ones, for example the 5,7-di-tert-butyl-3-phenyl-3H-benzofuran-2-one of formula C, comprises reacting the 2,4-di-tert-butylphenol of formula A with the mandelic acid of formula B, with elimination of water (q.v. U.S. Pat. No. 4,325,863, Example 1, column 8, lines 35–45).

For synthesising 3-phenyl-3H-benzofuran-2-ones which are substituted at the 3-phenyl ring or for preparing 3H-benzofuran-2-ones which are substituted in 3-position by a heterocycle, the drawback of the process is that it is necessary to use mandelic acids that are substituted at the phenyl ring or heterocyclic mandelic acids. However, not very many of these acids are known in the literature and the known syntheses for the preparation of these mandelic acids are quite troublesome.

Accordingly, the invention relates to a process for the preparation of compounds of formula I

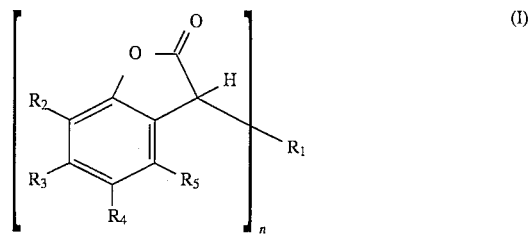

wherein, when n is 1, $R_1$ is an unsubstituted or substituted carbocyclic or heterocyclic aromatic ring system, when n is 2, $R_1$ is unsubstituted or $C_1$–$C_4$alkyl- or hydroxy-substituted phenylene or naphthylene; or is —$R_6$—X—$R_7$—, $R_2$, $R_3$, $R_4$ and $R_5$ are each independently of one another hydrogen, chloro, hydroxy, $C_1$–$C_{25}$alkyl, $C_7$–$C_9$-phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di-($C_1$–$C_4$alkyl)amino, $C_1$–$C_{25}$alkanoyloxy, $C_1$–$C_{25}$alkanoylamino, $C_3$–$C_{25}$alkenoyloxy, $C_3$–$C_{25}$alkanoyloxy which is interrupted by oxygen, sulfur or >N—$R_8$;

$C_6$–$C_9$cycloalkylcarbonyloxy, benzoyloxy or $C_1$–$C_{12}$alkyl-substituted benzoyloxy; or each pair of substituents $R_2$ and $R_3$ or $R_3$ and $R_4$ or $R_4$ and $R_5$, together with the linking carbon atoms, forms a benzene ring; $R_4$ is additionally —(CH$_2$)$_p$—COR$_9$ or —(CH$_2$)$_q$OH, or, if $R_3$ and $R_5$ are hydrogen, $R_4$ is additionally a radical of formula II

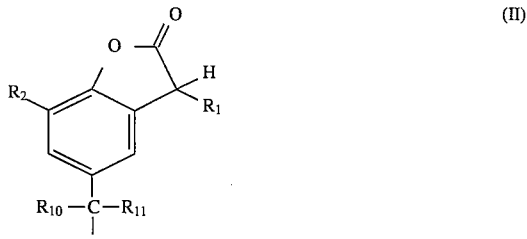

wherein $R_1$ is as defined above when n=1, $R_6$ and $R_7$ are each independently of the other unsubstituted or $C_1$–$C_4$alkyl-substituted phenylene or naphthylene, $R_8$ is hydrogen or $C_1$–$C_8$alkyl, $R_9$ is hydroxy,

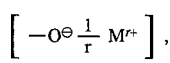, $C_1$–$C_{18}$ alkoxy or

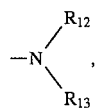, $R_{10}$ and $R_{11}$ are each independently of the other hydrogen, $CF_3$, $C_1$–$C_{12}$alkyl or phenyl, or $R_{10}$ and $R_{11}$, together with the linking carbon atom, form a $C_5$–$C_8$cycloalkylidene ring which is unsubstituted or substituted by 1 to 3 $C_1$–$C_4$alkyl groups, $R_{14}$ is hydrogen or $C_1$–$C_{18}$alkyl, M is a metal cation of valency r, X is a direct bond, oxygen, sulfur or $NR_{14}$, n is 1 or 2, p is 0, 1 or 2, q is 1, 2, 3, 4, 5 or 6, and r is 1, 2 or 3, which process comprises reacting a compound of formula III

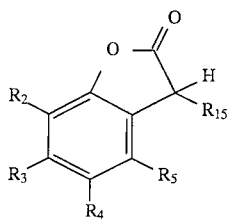 (III)

wherein $R_{15}$ is halogen or —$OR'_{15}$, $R'_{15}$ is hydrogen, $C_1$–$C_{25}$alkanoyl, $C_3$–$C_{25}$alkenoyl, $C_3$–$C_{25}$alkanoyl which is interrupted by oxygen, sulfur or >N—$R_8$; $C_6$–$C_9$cycloalkylcarbonyl, thenoyl, furoyl, benzoyl or $C_1$–$C_{12}$alkyl-substituted benzoyl; naphthoyl or $C_1$–$C_{12}$alkyl-substituted naphthoyl; $C_1$–$C_{25}$alkanesulfonyl, fluoro-substituted $C_1$–$C_{25}$alkanesulfonyl; phenylsulfonyl or $C_1$–$C_{12}$alkyl-substituted phenylsulfonyl;

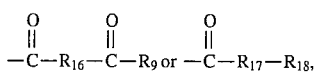

$R_{16}$ is a direct bond, $C_1$–$C_{18}$alkylene, $C_2$–$C_{18}$alkylene which is interrupted by oxygen, sulfur or >N—$R_8$; $C_2$–$C_{18}$alkenylene, $C_2$–$C_{20}$alkylidene, $C_7$–$C_{20}$phenylalkylidene, $C_5$–$C_8$cycloalkylene, $C_7$–$C_8$bicycloalkylene, unsubstituted or $C_1$–$C_4$alkyl-substituted phenylene,

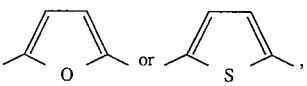

$R_{17}$ is oxygen, —NH— or

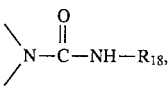

and $R_{18}$ is $C_1$–$C_{18}$alkyl or phenyl, with a compound of formula IV

—$R_1$  (IV).

Halogen substituents will conveniently be chloro, bromo or iodo. Chloro is preferred.

Alkanoyl of up to 25 carbon atoms inclusive is a branched or unbranched radical, typically including formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl. $R'_{15}$ defined as alkanoyl preferably contains 2 to 18, most preferably 2 to 12, e.g. 2 to 6, carbon atoms. Acetyl is particularly preferred.

$C_2$—$C_{25}$Alkanoyl substituted by a di($C_1$–$C_6$alkyl)phosphonate group will typically be $(CH_3CH_2O)_2POCH_2CO$—, $(CH_3O)_2POCH_2CO$—, $(CH_3CH_2CH_2CH_2O)_2POCH_2CO$—, $(CH_3CH_2O)_2POCH_2CH_2CO$—, $(CH_3O)_2POCH_2CH_2CO$—, $(CH_3CH_2CH_2CH_2O)_2POCH_2CH_2CO$—, $(CH_3CH_2O)_2PO(CH_2)_4CO$—, $(CH_3CH_2O)_2PO(CH_2)_8CO$— or $(CH_3CH_2O)_2PO(CH_2)_{17}CO$—.

Alkanoyloxy of up to 25 carbon atoms inclusive is an unbranched or branched radical and is typically formyloxy, acetoxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, eicosanoyloxy or docosanoyloxy. Alkanoyloxy of 2 to 18, preferably 2 to 12, e.g. 2 to 6, carbon atoms is preferred. Acetoxy is particularly preferred.

Alkenoyl of 3 to 25 carbon atoms is a branched or unbranched radical, typically including propenoyl, 2-butenoyl, 3-butenoyl, isobutenoyl, n-2,4-pentadienoyl, 3-methyl-2-butenoyl, n-2-octenoyl, n-2-dodecenoyl, isododecenoyl, oleoyl, n-2-octadecenoyl or n-4-octadecenoyl. Alkenoyl of 3 to 18, preferably 3 to 12, e.g. 3 to 6, most preferably 3 to 4, carbon atoms is preferred.

$C_3$–$C_{25}$Alkenoyl interrupted by oxygen, sulfur or >N—$R_8$ is typically $CH_3OCH_2CH_2CH=CHCO$— or $CH_3OCH_2CH_2OCH=CHCO$—.

Alkenoyloxy of 3 to 25 carbon atoms is a branched or unbranched radical, typically including propenoyloxy, 2-butenoyloxy, 3-butenoyloxy, isobutenoyloxy, n-2,4-pentadienoyloxy, 3-methyl-2-butenoyloxy, n-2-octenoyloxy, n-2-dodecenoyloxy, isododecenoyloxy, oleoyloxy, n-2-octadecenoyloxy or n-4-octadecenoyloxy. Alkenoyloxy of 3 to 18, preferably 3 to 12, typically 3 to 6, most preferably 3 to 4, carbon atoms is preferred.

$C_3$–$C_{25}$Alkenoyloxy interrupted by oxygen, sulfur or >N—$R_8$ will typically be $CH_3OCH_2CH_2CH=CHCOO$— or $CH_3OCH_2CH_2OCH=CHCOO$—.

$C_3$–$C_{25}$-Alkanoyl interrupted by oxygen, sulfur or >N—$R_8$ will typically be $CH_3$—O—$CH_2CO$—, $CH_3$—S—$CH_2CO$—, $CH_3$—NH—$CH_2CO$—, $CH_3$—N($CH_3$)—$CH_2CO$—, $CH_3$—O—$CH_2CH_2$—O—$CH_2CO$—, $CH_3$—(O—$CH_2CH_2$—)$_2$O—$CH_2CO$—, $CH_3$—(O—$CH_2CH_2$—)$_3$O—$CH_2CO$— or $CH_3$—(O—$CH_2CH_2$—)$_4$O—$CH_2CO$—.

$C_3$–$C_{25}$-Alkanoyloxy interrupted by oxygen, sulfur or >N—$R_8$ as will typically be $CH_3$—O—$CH_2COO$—, $CH_3$—S—$CH_2COO$—, $CH_3$—NH—$CH_2COO$—, $CH_3$—N($CH_3$)—$CH_2COO$—, $CH_3$—O—$CH_2CH_2$—O—$CH_2COO$—, $CH_3$—(O—$CH_2CH_2$—)$_2$O—$CH_2COO$—, $CH_3$—(O—$CH_2CH_2$—)$_3$O—$CH_2COO$— or $CH_3$—(O—$CH_2CH_2$—)$_4$O—$CH_2COO$—.

$C_6$–$C_9$Cycloalkylcarbonyl is typically cyclopentylcarbonyl, cyclohexylcarbonyl, cycloheptylcarbonyl or cyclooctylcarbonyl. Cyclohexylcarbonyl is preferred.

$C_6$–$C_9$Cycloalkylcarbonyloxy is typically cyclopentylcarbonyloxy, cyclohexylcarbonyloxy, cycloheptylcarbonyloxy or cyclooctylcarbonyloxy. Cyclohexylcarbonyloxy is preferred.

$C_1$–$C_{12}$Alkyl-substituted benzoyl which preferably carries 1 to 3, most preferably 1 or 2 alkyl groups, is typically o-, m- or p-methylbenzoyl, 2,3-dimethylbenzoyl, 2,4-dimethylbenzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4-tert-butylbenzoyl, 2-ethylbenzoyl, 2,4,6-trimethylbenzoyl, 2,6-dimethyl-4-tert-butylbenzoyl or 3,5-di-tert-butylbenzoyl. Preferred substituents are $C_1$–$C_8$alkyl, most preferably $C_1$–$C_4$alkyl.

$C_1$–$C_{12}$Alkyl-substituted benzoyloxy which preferably carries 1 to 3; most preferably 1 or 2 alkyl groups, is typically o-, m- or p-methylbenzoyloxy, 2,3-dimethylbenzoyloxy, 2,4-dimethylbenzoyloxy, 2,5-dimethylbenzoyloxy, 2,6-dimethylbenzoyloxy, 3,4-dimethylbenzoyloxy, 3,5-dimethylbenzoyloxy, 2-methyl-6-ethylbenzoyloxy, 4-tert-butylbenzoyloxy, 2-ethylbenzoyloxy, 2,4,6-trimethylbenzoyloxy, 2,6-dimethyl-4-tert-butylbenzoyloxy or 3,5-di-tert-butylbenzoyloxy. Preferred substituents are $C_1$–$C_8$alkyl, preferably $C_1$–$C_4$alkyl.

$C_1$–$C_{12}$Alkyl-substituted naphthoyl, which is 1-naphthoyl or 2-naphthoyl and preferably contains 1 to 3, most preferably 1 or 2 alkyl groups, will typically be 1-, 2-, 3-, 4-, 5-, 6-, 7- or 8-methylnaphthoyl, 1-, 2-, 3-, 4-, 5-, 6-, 7- or 8-ethylnaphthoyl, 4-tert-butylnaphthoyl or 6-tert-butylnaphthoyl. Particularly preferred substituents are $C_1$–$C_8$alkyl, most preferably $C_1$–$C_4$alkyl.

$C_1$–$C_{25}$Alkanesulfonyl is a branched or unbranched radical, typically methanesulfonyl, ethanesulfonyl, propanesulfonyl, butanesulfonyl, pentanesulfonyl, hexanesulfonyl, heptanesulfonyl, octanesulfonyl, nonanesulfonyl or docosanesulfonyl. Alkanesulfonyl of 1 to 18, preferably 1 to 12, e.g. 2 to 6, carbon atoms is preferred. Methanesulfonyl is particularly preferred.

Fluoro-substituted $C_1$–$C_{25}$alkanesulfonyl is typically trifluoromethanesulfonyl.

$C_1$–$C_{12}$Alkyl-substituted phenylsulfonyl which carries preferably 1 to 3, most preferably 1 or 2, alkyl groups is typically o-, m- or p-methylphenylsulfonyl, p-ethylphenylsulfonyl, p-propylphenylsulfonyl or p-butylphenylsulfonyl. Preferred substituents are $C_1$–$C_8$alkyl, most preferably $C_1$–$C_4$alkyl. p-Methylphenylsulfonyl is particularly preferred.

Alkyl of up to 25 carbon atoms is a branched or unbranched radical and is typically methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. A preferred meaning of $R_2$ and $R_4$ is typically $C_1$–$C_{18}$alkyl. A particularly preferred meaning of $R_4$ is $C_1$–$C_4$alkyl.

Alkenyl of 3 to 25 carbon atoms is a branched or unbranched radical, typically including propenyl, 2-butenyl, 3-butenyl, isobutenyl, n-2,4-pentadienyl, 3-methyl-2-butenyl, n-2octenyl, n-2-dodecenyl, isododecenyl, oleyl, n-2-octadecenyl or n-4-octadecenyl. Alkenyl of 3 to 18, preferably 3 to 12, typically 3 to 6, most preferably 3 to 4, carbon atoms is preferred.

Alkenyloxy of 3 to 25 carbon atoms is a branched or unbranched radical, typically including propenyloxy, 2-butenyloxy, 3-butenyloxy, isobutenyloxy, n-2,4-pentadienyloxy,-3-methyl-2-butenyloxy, n-2-octenyloxy, n-2-dodecenyloxy, isododecenyloxy, oleyloxy, n-2-octadecenyloxy or n-4-octadecenyloxy. Alkenyloxy of 3 to 18, preferably 3 to 12, typically 3 to 6, most preferably 3 to 4, carbon atoms is preferred.

Alkynyl of 3 to 25 carbon atoms is a branched or unbranched radical, typically including propynyl ($—CH_2—C{\equiv}CH$), 2-butynyl, 3-butynyl, n-2-octynyl or n-2-dodecynyl. Alkynyl of 3 to 18, preferably 3 to 12, typically 3 to 6, most preferably 3 to 4, carbon atoms is preferred.

Alkynyloxy of 3 to 25 carbon atoms is a branched or unbranched radical, typically including propynyloxy ($—OCH_2—C{\equiv}CH$), 2-butynyloxy, 3-butynyloxy, n-2-octynyloxy, or n-2-dodecynyloxy. Alkynyloxy of 3 to 18, preferably 3 to 12, typically 3 to 6, most preferably 3 to 4, carbon atoms is preferred.

$C_2$–$C_{25}$-Alkyl interrupted by oxygen, sulfur or $>N—R_8$ will typically be $CH_3—O—CH_2—$, $CH_3—S—CH_2—$, $CH_3—NH—CH_2—$, $CH_3—N(CH_3)—CH_2—$, $CH_3—O—CH_2CH_2—O—CH_2—$, $CH_3—(O—CH_2CH_2 13\ )_2O—CH_2—$, $CH_3—(O—CH_2CH_2—)_3O—CH_2—$ or $CH_3—(O—CH_2CH_2—)_4O—CH_2—$.

$C_7$–$C_9$Phenylalkyl may typically be benzyl, α-methylbenzyl, α,α-dimethylbenzyl or 2-phenylethyl. Benzyl and α,α-dimethylbenzyl are preferred.

$C_7$–$C_9$-Phenylalkyl which is unsubstituted or substituted in the phenyl moiety by 1 to 3 $C_1$–$C_4$alkyl groups will typically be benzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tertbutylbenzyl. Benzyl is preferred.

$C_7$–$C_{25}$Phenylalkyl which is interrupted by oxygen, sulfur or $>N—R_8$ and is unsubstituted or substituted in the phenyl moiety by 1 to 3 $C_1$–$C_4$alkyl groups is a branched or unbranched radical such as phenoxymethyl, 2-methylphenoxymethyl, 3-methylphenoxymethyl, 4-methylphenoxymethyl, 2,4-dimethylphenoxymethyl, 2,3-dimethylphenoxymethyl, phenylthiomethyl, N-methyl-N-phenyl-methyl, N-ethyl-N-phenylmethyl, 4-tertbutylphenoxymethyl, 4-tertbutylphenoxyethoxymethyl, 2,4-di-tert-butylphenoxymethyl, 2,4-di-tert-butylphenoxyethoxymethyl, phenoxyethoxyethoxymethyl, benzyloxymethyl, benzyloxyethoxymethyl, N-benzyl-N-ethylmethyl or N-benzyl-N-isopropylmethyl.

$C_7$–$C_9$Phenylalkoxy is typically benzyloxy, α-methylbenzyloxy, α,α-dimethylbenzyloxy or 2-phenylethoxy. Benzyloxy is preferred.

$C_1$—$C_4$Alkyl-substituted phenyl that preferably contains 1 to 3, preferably 1 or 2, alkyl groups, will typically be o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

$C_1$–$C_4$Alkyl-substituiertes phenoxy which preferably contains 1 to 3, most preferably 1 or 2, alkyl groups, is typically o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5dimethylphenoxy, 2-methyl-6-ethylphenoxy, 4-tert-butylphenoxy, 2-ethylphenoxy or 2,6-diethylphenoxy.

Unsubstituted or $C_1$–$C_4$alkyl-substituted $C_5$–$C_8$cycloalkyl is typically cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Cyclohexyl and tertbutylcyclohexyl are preferred.

Unsubstituted or $C_1$–$C_4$alkyl-substituted $C_5$–$C_8$cycloalkoxy is typically cyclopentoxy, methylcyclopentoxy, dimethylcyclopentoxy, cyclohexoxy, methylcyclohexoxy, dimethylcyclohexoxy, trimethylcyclohexoxy, tert-butylcyclohexoxy, cycloheptoxy or cyclooctoxy. Cyclohexoxy and tert-butylcyclohexoxy are preferred.

Alkoxy of up to 25 carbon atoms is a branched or unbranched radical and is typically methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. Alkoxy of 1 to 12, preferably 1 to 8, e.g. 1 to 6, carbon atoms is preferred.

$C_2$–$C_{25}$Alkoxy interrupted by oxygen, sulfur or >N—$R_8$ is typically $CH_3$—O—$CH_2O$—, $CH_3$—S—$CH_2CH_2O$—, $CH_3$—NH—$CH_2CH_2O$—, $CH_3$—N($CH_3$)—$CH_2CH_2O$—, $CH_3$—O—$CH_2CH_2$—O—$CH_2CH_2O$—, $CH_3$—(O—$CH_2CH_2$—)$_2$O—$CH_2CH_2O$—, $CH_3$—(O—$CH_2CH_2$—)$_3$O—$CH_2CH_2O$— or $CH_3$—(O—$CH_2CH_2$—)$_4$O—$CH_2CH_2O$—, Alkylthio of up to 25 carbon atoms is a branched or unbranched radical and is typically methylthio, ethylthio, propylthio, isopropylthio, n-butylthio, isobutylthio, pentylthio, isopentylthio, hexylthio, heptylthio, octylthio, decylthio, tetradecylthio, hexadecylthio or octadecylthio. Alkylthio of 1 to 12, preferably 1 to 8, e.g. 1 to 6, carbon atoms is preferred.

Alkylamino of up to 4 carbon atoms is a branched or unbranched radical and is typically methylamino, ethylamino, propylamino, isopropylamino, n-butylamino, isobutylamino or tert-butylamino.

Di($C_1$–$C_4$)alkylamino also signifies that the two moieties, each independently of the other, are branched or unbranched, and is typically dimethylamino, methylethylamino, diethylamino, methyl-n-propylamino, methylisopropylamino, methyl-n-butylamino, methylisobutylamino, ethylisopropylamino, ethyl-n-butylamino, ethylisobutylamino, ethyl-tert-butyl-amino, diethylamino, diisopropylamino, isopropyl-n-butylamino, isopropylisobutylamino, di-n-butylamino or diisobutylamino.

Alkanoylamino of up to 25 carbon atoms is an unbranched or branched radical and is typically formylamino, acetylamino, propionylamino, butanoylamino, pentanoylamino, hexanoylamino, heptanoylamino, octanoylamino, nonanoylamino, decanoylamino, undecanoylamino, dodecanoylamino, tridecanoylamino, tetradecanoylamino, pentadecanoylamino, hexadecanoylamino, heptadecanoylamino, octadecanoylamino, eicosanoylamino oder docosanoylamino. Alkanoylamino of 2 to 18, preferably 2 to 12, e.g. 2 to 6, carbon atoms is preferred.

$C_1$–$C_{18}$Alkylene is a branched or unbranched radical, typically methylene, ethylene, propylene, trimethylene, tetramethylene, pentamethylene, hexamethylene, heptamethylene, octamethylene, decamethylene, dodecamethylene or octadecamethylene. $C_1$–$C_{12}$Alkylene is preferred, and $C_1$–$C_8$alkylene is particularly preferred.

A $C_1$–$C_4$alkyl-substituted $C_5$–$C_{12}$cycloalkylene ring which preferably contains 1 to 3, preferably 1 or 2 branched or unbranched alkyl groups will typically be cyclopentylene, methylcyclopentylene, dimethylcyclopentylene, cyclohexylene, methylcyclohexylene, dimethylcyclohexylene, trimethylcyclohexylene, tert-butylcyclohexylene, cycloheptylene, cyclooctylene or cyclodecylene. Cyclohexylene and tert-butylcyclohexylene.

$C_2$–$C_{18}$Alkylene which is interrupted by oxygen, sulfur or >N—$R_8$ will typically be —$CH_2$—O—$CH_2$—, —$CH_2$—S—$CH_2$—, —$CH_2$—NH—$CH_2$—, —$CH_2$—N($CH_3$)—$CH_2$, —$CH_2$—O—$CH_2CH_2$—O—$CH_2$—, —$CH_2$—(O—$CH_2CH_2$—)$_2$O—$CH_2$—, —$CH_2$—(O—$CH_2CH_2$—)$_3$—O—$CH_2$—, —$CH_2$—(O—$CH_2CH_2$—)$_4$O—$CH_2$— or —$CH_2CH_2$—S—$CH_2$—.

$C_2$—$C_{18}$Alkenylene is typically vinylene, methylvinylene, octenylethylene or dodecenylethylene. $C_2$–$C_8$Alkenylene is preferred.

Alkylidene of 2 to 20 carbon atoms may typically be ethylidene, propyliden, butylidene, pentylidene, 4-methylpentylidene, heptylidene, nonylidene, tridecylidene, nonadecylidene, 1-methylethylidene, 1-ethylpropylidene or 1-ethylpentylidene. $C_2$—$C_8$Alkylidene is preferred.

Phenylalkylidene of 7 to 20 carbon atoms may typically be benzylidene, 2-phenylethylidene or 1-phenyl-2-hexylidene. $C_7$–$C_9$Phenylalkylidene is preferred.

$C_5$–$C_8$Cycloalkylene is a saturated hydrocarbon group having two free valences and at least one ring unit and is typically cyclopentylene, cyclohexylene, cycloheptylene or cyclooctylene. Cyclohexylene is preferred.

$C_7$–$C_8$Bicycloalkylene may be bicycloheptylene or bicyclooctylene.

Unsubstituted or $C_1$–$C_4$alkyl-substituted phenylene or naphthylene is typically 1,2-, 1,3-, 1,4-phenylene, 1,2-, 1,3-, 1,4-, 1,6-, 1,7-, 2,6- or 2,7-naphthylene. 1,4-phenylene is preferred.

A $C_1$–$C_4$alkyl-substituted $C_5$–$C_8$cycloalkylidene ring that preferably contains 1 to 3, most preferably 1 or 2, branched or unbranched alkyl groups, is typically cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cycloheptylidene or cyclooctylidene. Cyclohexylidene and tert-butylcyclohexylidene are preferred.

A mono-, di- or trivalent metal cation is preferably an alkali metal cation, an alkaline earth metal cation or an aluminium cation, typically $Na^+$, $K^+$, $Mg^{++}$, $Ca^{++}$ or $Al^{+++}$.

$R_1$ (if n=1) may be any aromatic, carbocyclic or heterocyclic ring system which is unsubstituted or substituted.

Suitable carbocyclic ring systems are based on a benzene ring, or on a system of fused benzene rings, typically of 2 to 5, preferably 2 or 3, rings, one or more of which rings may be wholly or partially hydrogenated. It is essential that the linkage to the benzofuranone is through an aromatic ring. Heterocyclic rings, which may themselves be aromatic or nonaromatic, may also be fused to the benzene ring or the fused benzene rings, preferably those containing 5 or 6 ring members, typically 1 to 3 hetero atoms selected from the group consisting of nitrogen, oxygen and sulfur.

Suitable heterocyclic aromatic ring systems are preferably 5- or 6-membered heterocyclic rings having aromaticity, which contain 1 to 3, preferably 1 or 2, hetero atoms selected from the group consisting of nitrogen, oxygen and sulfur. To these rings may be fused further carbocyclic or heterocyclic aromatic or non-aromatic rings, carbocyclic 6-membered, preferably aromatic, rings being preferred.

Possible substituents for the aromatic radical $R_1$ (n=1) typically include those defined in connection with the substituents $R_{19}$ to $R_{23}$. Such substituents are preferably chloro, amino, hydroxy, $C_1$–$C_{18}$alkyl, $C_1$–$C_{18}$alkoxy, $C_1$–$C_{18}$alkylthio, $C_3$–$C_4$alkenyloxy, $C_3$–$C_4$alkynyloxy, $C_1$–$C_4$alkylamino, di($C_1$–$C_4$alkyl)amino, phenyl, benzyl, benzoyl or benzoyloxy, preferably chloro, amino, hydroxy, $C_1$–$C_4$alkyl, $C_1$–$C_4$alkoxy, $C_1$–$C_4$alkylthio, $C_1$–$C_4$alkylamino or di($C_1$–$C_4$alkyl)amino.

An interesting process is that for the preparation of compounds of formula I, wherein, if n is 1, $R_1$ is an unsubstituted or substituted 5- or 6-membered aromatic ring to which further rings may be fused.

Also of interest is a process for the preparation of compounds of formula I, wherein, if n is 1, $R_1$ is unsubstituted or substituted phenyl, naphthyl, phenanthryl, anthryl, 5,6,7,8-tetrahydro-2-naphthyl, thienyl, benzo[b]thienyl, naphtho[2,3-b]thienyl, thiathrenyl, furyl, benzofuryl, isobenzofuryl, dibenzofuryl, chromenyl, xanthenyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, tetralinyl, fluorenyl or phenoxazinyl. Preferred substituents of the above heterocyclic ring systems are chloro, amino, hydroxy, $C_1$–$C_4$alkyl, $C_1$–$C_4$alkoxy, $C_1$–$C_4$alkylthio, $C_1$–$C_4$alkylamino or di($C_1$–$C_4$alkyl)amino.

A particularly interesting process is that for the preparation of compounds of formula I, wherein, when n is 1, $R_1$ is phenanthryl, thienyl, dibenzofuryl, unsubstituted or $C_1$–$C_4$alkyl-substituted carbazolyl; or is fluorenyl, or $R_1$ is a radical of formula V or VI

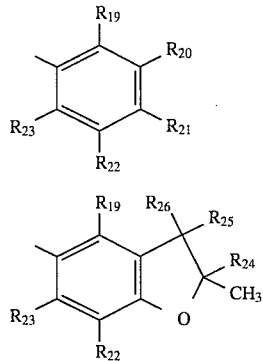

wherein $R_{19}$, $R_{20}$, $R_{21}$, $R_{22}$ and $R_{23}$ are each independently of one another hydrogen, halogen, hydroxy, $C_1$–$C_{25}$alkyl, $C_2$–$C_2$alkyl which is interrupted by oxygen, sulfur or >N—$R_8$;

$C_1$–$C_{25}$alkoxy, $C_2$–$C_{25}$alkoxy which is interrupted by oxygen, sulfur or >N—$R_8$; $C_1$–$C_{25}$-alkylthio, $C_3$–$C_{25}$alkenyl, $C_3$–$C_{25}$alkenyloxy, $C_3$–$C_{25}$alkynyl, $C_3$–$C_{25}$alkynyloxy, $C_7$–$C_9$phenylalkyl, $C_7$–$C_9$phenylalkoxy, unsubstituted or $C_1$–$C_4$alkyl-substituted phenyl; unsubstituted or $C_1$–$C_4$alkyl-substituted phenoxy; unsubstituted or $C_1$–$C_4$alkyl-substituted $C_5$–$C_8$-cycloalkyl; unsubstituted or $C_1$–$C_4$alkyl-substituted $C_5$–$C_8$cycloalkoxy; $C_1$–$C_4$alkylamino, di($C_1$–$C_4$alkyl)amino, $C_1$–$C_{25}$alkanoyl, $C_3$–$C_{25}$alkanoyl which is interrupted by oxygen, sulfur or >N—$R_8$; $C_1$–$C_{25}$-alkanoyloxy, $C_3$–$C_{25}$alkanoyloxy which is interrupted by oxygen, sulfur or >N—$R_8$; $C_1$–$C_{25}$alkanoylamino, $C_3$–$C_{25}$alkenoyl, $C_3$–$C_{25}$alkenoyl which is interrupted by oxygen, sulfur or >N—$R_8$; $C_3$–$C_{25}$alkenoyloxy, $C_3$–$C_{25}$alkenoyloxy which is interrupted by oxygen, sulfur or >N—$R_8$; $C_6$–$C_9$cycloalkylcarbonyl, $C_6$–$C_9$cycloalkylcarbonyloxy, benzoyl or $C_1$–$C_{12}$alkyl-substituted benzoyl; benzoyloxy or $C_1$–$C_{12}$alkyl-substituted benzoyloxy;

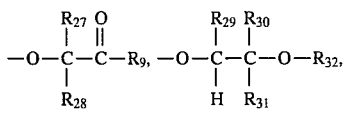

or in formula V each pair of substituents $R_{19}$ and $R_{20}$ or $R_{20}$ and $R_2$, together with the linking carbon atoms, forms a benzene ring, $R_{24}$ is hydrogen, $C_1$–$C_4$alkyl, unsubstituted or $C_1$–$C_4$alkyl-substituted phenyl, $R_{25}$ and $R_{26}$ are hydrogen, $C_1$–$C_4$alkyl or phenyl, with the proviso that at least one of $R_{25}$ and $R_{26}$ is hydrogen, $R_{27}$ and $R_{28}$ are each independently of the other hydrogen, $C_1$–$C_4$alkyl or phenyl, $R_{29}$ is hydrogen or $C_1$–$C_4$alkyl, $R_{30}$ is hydrogen, unsubstituted or $C_1$–$C_4$alkyl-substituted phenyl; $C_1$–$C_{25}$alkyl, $C_2$–$C_{25}$alkyl which is interrupted by oxygen, sulfur or >N—$R_8$; $C_7$–$C_9$phenylalkyl which is unsubstituted or substituted at the phenyl moiety by 1 to 3 $C_1$–$C_4$alkyl groups; $C_7$–$C_{25}$phenylalkyl which is interrupted by oxygen, sulfur or >N—$R_8$ or is unsubstituted or substituted in the phenyl moiety by 1 to 3 $C_1$–$C_4$alkyl groups; or $R_{29}$ and $R_{30}$, together with the linking carbon atoms, form a $C_5$–$C_{12}$cycloalkylene ring which is unsubstituted or substituted by 1 to 3 $C_1$–$C_4$alkyl groups, $R_{31}$ is hydrogen or $C_1$–$C_4$alkyl, $R_{32}$ is hydrogen, $C_1$–$C_{25}$alkanoyl, $C_3$–$C_{25}$alkenoyl, $C_3$–$C_{25}$alkanoyl which is interrupted by oxygen, sulfur or >N—$R_8$; $C_2$–$C_{25}$alkanoyl which is substituted by a di($C_1$–$C_6$alkyl)-phosphonate group; $C_6$–$C_9$cycloalkylcarbonyl, thenoyl, furoyl, benzoyl or $C_1$–$C_{12}$alkyl-substituted benzoyl;

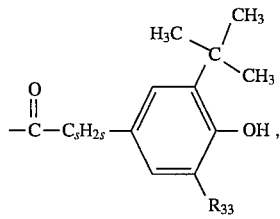

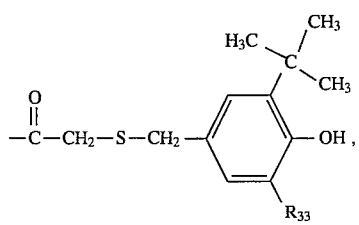

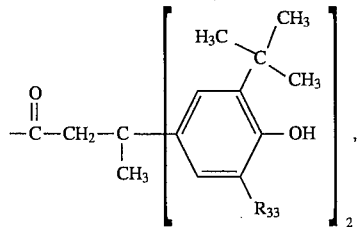

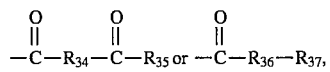

$R_{33}$ is hydrogen or $C_1$–$C_8$alkyl, $R_{34}$ is a direct bond, $C_1$–$C_{18}$alkylene, $C_2$–$C_{18}$alkylene which is interrupted by oxygen, sulfur or >N—$R_8$; $C_2$–$C_{18}$alkenylene, $C_2$–$C_{20}$alkylidene, $C_7$–$C_{20}$phenylalkylidene, $C_5$–$C_8$cycloalkylene, $C_7$–$C_8$bicycloalkylene, unsubstituted or $C_1$–$C_4$alkyl-substituted phenylene,

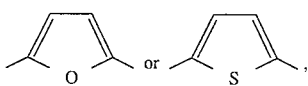 , $R_{35}$ is hydroxy,

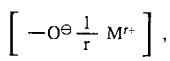 , $C_1$–$C_{18}$alkoxy or

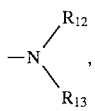 , $R_{36}$ is oxygen, —NH— or

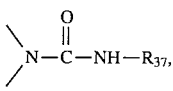 , $R_{37}$ is $C_1$–$C_{18}$alkyl or phenyl, and s is 0, 1 or 2.

Also of particular interest is a process for the preparation of compounds of formula I, wherein, when n is 2, $R_1$ is —$R_6$—X—$R_7$—, $R_6$ and $R_7$ are phenylene, X is oxygen or —$NR_{14}$—, and $R_{14}$ is $C_1$–$C_4$alkyl.

A process of very particular interest is that for the preparation of compounds of formula I, wherein, when n is 1, $R_1$ is phenanthryl, thienyl, dibenzofuryl, unsubstituted or $C_1$–$C_4$alkyl-substituted carbazolyl; or is fluorenyl, or $R_1$ is a radical of formula V or VI

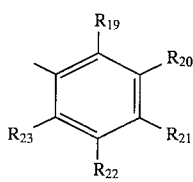 (V)

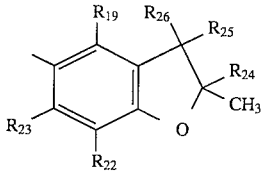 (VI)

wherein $R_9$, $R_{20}$, $R_{21}$, $R_{22}$ and $R_{23}$ are each independently of one another hydrogen, halogen, hydroxy, $C_1$–$C_{18}$alkyl, $C_2$–$C_{18}$alkyl which is interrupted by oxygen, sulfur or >N—$R_8$;

$C_1$–$C_{18}$alkoxy, $C_2$–$C_{18}$alkoxy which is interrupted by oxygen, sulfur or >N—$R_8$; $C_1$–$C_{18}$-alkylthio, $C_3$–$C_{18}$alkenyl, $C_3$–$C_{18}$alkenyloxy, $C_3$–$C_{18}$alkynyl, $C_3$–$C_{18}$alkynyloxy, $C_7$–$C_9$-phenylalkyl, $C_7$–$C_9$phenylalkoxy, unsubstituted or $C_1$–$C_4$alkyl-substituted phenyl; unsubstituted or $C_1$–$C_4$alkyl-substituted phenoxy; unsubstituted or $C_1$–$C_4$alkyl-substituted $C_5$–$C_8$-cycloalkyl; unsubstituted or $C_1$–$C_4$alkyl-substituted $C_5$–$C_8$cycloalkoxy; $C_1$–$C_4$alkylamino, di($C_1$–$C_4$alkyl)amino, $C_1$–$C_{18}$alkanoyl, $C_3$–$C_{18}$alkanoyl which is interrupted by oxygen, sulfur or >N—$R_8$; $C_1$–$C_{18}$-alkanoyloxy, $C_3$–$C_{18}$alkanoyloxy which is interrupted by oxygen, sulfur or >N—$R_8$; $C_1$–$C_{18}$alkanoylamino, $C_3$–$C_{18}$alkenoyl, $C_3$–$C_{18}$alkenoyl which is interrupted by oxygen, sulfur or >N—$R_8$; $C_3$–$C_{18}$alkenoyloxy, $C_3$–$C_{18}$alkenoyloxy which is interrupted by oxygen, sulfur or >N—$R_8$; $C_6$–$C_9$cycloalkylcarbonyl, $C_6$–$C_9$cycloalkylcarbonyloxy, benzoyl or $C_1$–$C_{12}$alkyl-substituted benzoyl; benzoyloxy or $C_1$–$C_8$alkyl-substituted benzoyloxy;

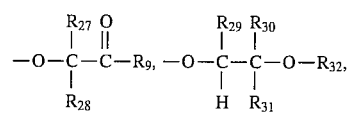

or in formula V each pair of substituents $R_{19}$ and $R_{20}$ or $R_{20}$ and $R_{21}$, together with the linking carbon atoms, forms a benzene ring, $R_{24}$ is hydrogen, $C_1$–$C_4$alkyl, unsubstituted or $C_1$–$C_4$alkyl-substituted phenyl, $R_{25}$ and $R_{26}$ are hydrogen, $C_1$–$C_4$alkyl or phenyl, with the proviso that at least one of $R_{25}$ and $R_{26}$ is hydrogen, $R_{27}$ and $R_{28}$ are each independently of the other hydrogen, $C_1$–$C_4$alkyl or phenyl, $R_{29}$ is hydrogen or $C_1$–$C_4$alkyl, $R_{30}$ is hydrogen, unsubstituted or $C_1$–$C_4$alkyl-substituted phenyl; $C_1$–$C_{18}$alkyl, $C_2$–$C_{18}$alkyl which is interrupted by oxygen, sulfur or >N×$R_8$; $C_7$–$C_9$phenylalkyl which is unsubstituted or substituted in the phenyl moiety by 1 to 3 $C_1$–$C_4$alkyl groups; $C_7$–$C_{18}$phenylalkyl which is interrupted by oxygen, sulfur or >N—$R_8$ or is unsubstituted or substituted at the phenyl moiety by 1 to 3 $C_1$–$C_4$alkyl groups; or $R_{29}$ and $R_{30}$, together with the linking carbon atoms, form a $C_5$–$C_9$cycloalkylene ring which is unsubstituted or substituted by 1 to 3 $C_1$–$C_4$alkyl groups, $R_{31}$ is hydrogen or $C_1$–$C_4$alkyl, $R_{32}$ is hydrogen, $C_1$–$C_{18}$alkanoyl, $C_3$–$C_{18}$alkenoyl, $C_3$–$C_{18}$alkanoyl which is interrupted by oxygen, sulfur or >N—$R_8$; $C_2$–$C_{18}$alkanoyl which is substituted by a di($C_1$–$C_6$alkyl)-phosphonate group; $C_6$–$C_9$cycloalkylcarbonyl, thenoyl, furoyl, benzoyl or $C_1$–$C_8$alkyl-substituted benzoyl;

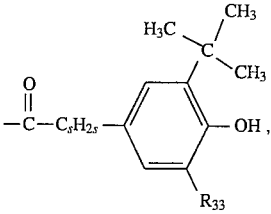

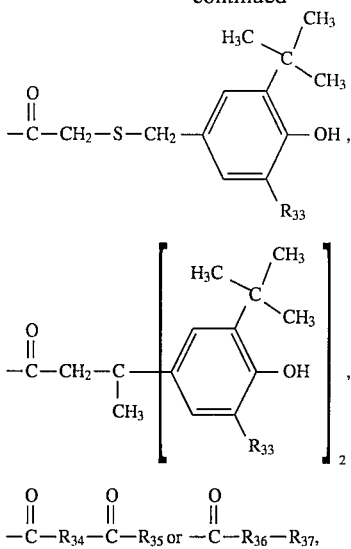

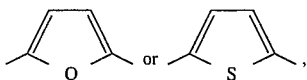

$R_{33}$ is hydrogen or $C_1$–$C_8$alkyl, $R_{34}$ is a direct bond, $C_1$–$C_{18}$alkylene, $C_2$–$C_{12}$alkylene which is interrupted by oxygen, sulfur or >N—$R_8$, $C_2$–$C_{12}$alkenylene, $C_2$–$C_{12}$alkylidene, $C_7$–$C_{12}$phenylalkylidene, $C_5$–$C_8$cycloalkylene, $C_7$–$C_8$bicycloalkylene, unsubstituted or $C_1$–$C_4$alkyl-substituted phenylene,

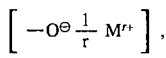

$R_{35}$ is hydroxy, $$\left[ -O^{\ominus} \frac{1}{r} M^{r+} \right],$$

$C_1$–$C_{18}$alkoxy or

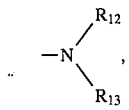

$R_{36}$ is oxygen, —NH— or

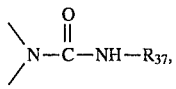

$R_{37}$ is $C_1$–$C_{18}$alkyl or phenyl, and s is 0, 1 or 2.

A preferred process is a process for the preparation of compounds of formula I, wherein $R_{19}$, $R_{20}$, $R_{21}$, $R_{22}$ and $R_{23}$ are each independently of one another hydrogen, chloro, bromo, hydroxy, $C_1$–$C_{18}$alkyl, $C_2$–$C_{18}$alkyl which is interrupted by oxygen or sulfur; $C_1$–$C_{18}$alkoxy, $C_2$–$C_{18}$alkoxy which is interrupted by oxygen or sulfur; $C_1$–$C_{18}$alkylthio, $C_3$–$C_{12}$alkenyloxy, $C_3$–$C_{12}$alkynyloxy, $C_7$–$C_9$phenylalkyl, $C_7$–$C_9$phenylalkoxy, unsubstituted or $C_1$–$C_4$alkyl-substituted phenyl; phenoxy, cyclohexyl, $C_5$–$C_8$cycloalkoxy; $C_1$–$C_4$-alkylamino, di($C_1$–$C_4$alkyl)amino, $C_1$–$C_{12}$alkanoyl, $C_3$–$C_{12}$alkanoyl which is interrupted by oxygen or sulfur; $C_1$–$C_{12}$alkanoyloxy, $C_3$–$C_{12}$alkanoyloxy which is interrupted by oxygen or sulfur; $C_1$–$C_{12}$alkanoylamino, $C_3$–$C_{12}$alkenoyl, $C_3$–$C_{12}$alkenoyloxy, cyclohexylcarbonyl, cyclohexylcarbonyloxy, benzoyl or $C_1$–$C_4$alkyl-substituted benzoyl; benzoyloxy or $C_1$–$C_4$-alkyl substituted benzoyloxy;

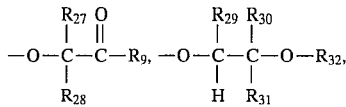

or in formula V each pair of substituents $R_{19}$ and $R_{20}$ or $R_{20}$ and $R_{21}$, together with the linking carbon atoms, forms a benzene ring, $R_{24}$ is hydrogen or $C_1$–$C_4$alkyl, $R_{25}$ and $R_{26}$ are hydrogen or $C_1$–$C_4$alkyl, with the proviso that at least one of $R_{25}$ and $R_{26}$ is hydrogen, $R_{27}$ and $R_{28}$ are each independently of the other hydrogen or $C_1$–$C_4$alkyl, $R_{29}$ is hydrogen, $R_{30}$ is hydrogen, phenyl, $C_1$–$C_{18}$alkyl, $C_2$–$C_{18}$alkyl which is interrupted by oxygen or sulfur; $C_7$–$C_9$phenylalkyl, $C_7$–$C_{18}$phenylalkyl which is interrupted by oxygen or sulfur and unsubstituted or substituted in the phenyl moiety by 1 to 3 $C_1$–$C_4$alkyl groups, and $R_{29}$ and $R_{30}$, together with the linking carbon atoms, form a cyclohexylene ring which is unsubstituted or substituted by 1 to 3 $C_1$–$C_4$alkyl groups, $R_{31}$ is hydrogen or $C_1$–$C_4$alkyl, $R_{32}$ is hydrogen, $C_1$–$C_{18}$alkanoyl, $C_3$–$C_{12}$alkenoyl, $C_3$–$C_{12}$alkanoyl which is interrupted by oxygen or sulfur; $C_2$–$C_{12}$alkanoyl which is substituted by a di($C_1$–$C_6$-alkyl)phosphonate group; $C_6$–$C_9$cycloalkylcarbonyl, benzoyl,

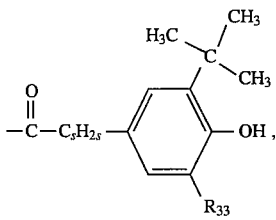

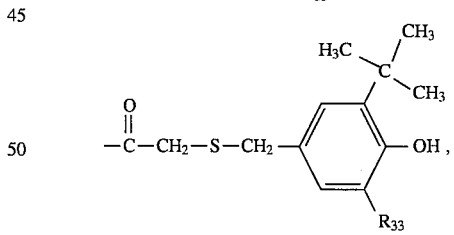

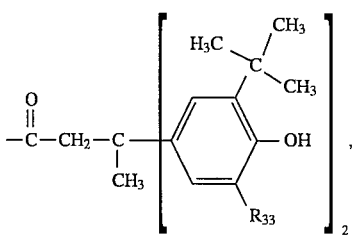

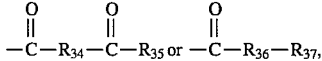

$R_{33}$ is hydrogen or $C_1$–$C_4$alkyl, $R_{34}$ is $C_1$–$C_{12}$alkylene, $C_2$–$C_8$alkenylene, $C_2$–$C_8$alkylidene, $C_7$–$C_{12}$phenylalkylidene, $C_5$–$C_8$cycloalkylene or phenylene, $R_{35}$ is hydroxy,

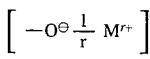

or $C_1$–$C_{18}$alkoxy, $R_{36}$ is oxygen or —NH—, $R_{37}$ is $C_1$–$C_8$alkyl or phenyl, and s is 1 or 2.

Also preferred is a process for the preparation of compounds of formula I, wherein $R_1$ is phenanthryl, thienyl, dibenzofuryl, unsubstituted or $C_1$–$C_4$alkyl-substituted carbazolyl; or fluorenyl, or $R_1$ is a radical of formula V

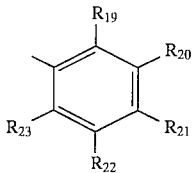

wherein $R_{19}$, $R_{20}$, $R_{21}$, $R_{22}$ and $R_{23}$ are each independently of one another hydrogen, chloro, hydroxy, $C_1$–$C_{18}$alkyl, $C_1$–$C_{18}$alkoxy, $C_1$–$C_{18}$alkylthio, $C_3$–$C_4$alkenyloxy, $C_3$–$C_4$-alkynyloxy, phenyl, benzoyl, benzoyloxy or

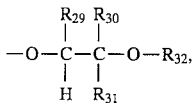

$R_{29}$ is hydrogen, $R_{30}$ is hydrogen, phenyl or $C_1$–$C_{18}$alkyl, or $R_{29}$ and $R_{30}$, together with the linking carbon atoms, form a cyclohexylene ring which is unsubstituted or substituted by 1 to 3 $C_1$–$C_4$-alkyl groups, $R_{31}$ is hydrogen or $C_1$–$C_4$alkyl, and $R_{32}$ is hydrogen, $C_1$–$C_{12}$alkanoyl or benzoyl.

An especially preferred process is a process for the preparation of compounds of formula I, wherein $R_{19}$ is hydrogen or $C_1$–$C_4$alkyl, $R_{20}$ is hydrogen or $C_1$–$C_4$alkyl, $R_{21}$ is hydrogen, chloro, hydroxy, $C_1$–$C_{12}$alkyl, $C_1$–$C_4$alkoxy, $C_1$–$C_4$alkylthio, phenyl or —O—$CH_2$—$CH_2$—O—$R_{32}$, $R_{22}$ is hydrogen or $C_1$–$C_4$alkyl, $R_{23}$ is hydrogen or $C_1$–$C_4$alkyl, and $R_{32}$ is $C_1$–$C_4$alkanoyl.

A very particularly preferred process is that for the preparation of compounds of formula I, wherein $R_2$, $R_3$, $R_4$ and $R_5$ are each independently of one another chloro, hydroxy, $C_1$–$C_{25}$alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{12}$alkoxy, $C_1$–$C_{12}$alkylthio, $C_1$–$C_4$alkylamino, di($C_1$–$C_4$alkyl)amino, $C_1$–$C_{18}$alkanoyloxy, $C_1$–$C_{18}$alkanoylamino, $C_3$–$C_{18}$alkenoyloxy, $C_3$–$C_{18}$alkanoyloxy which is interrupted by oxygen, sulfur or >N—$R_8$; $C_6$–$C_9$cycloalkylcarbonyloxy, benenzoyloxy or $C_1$–$C_8$alkyl-substituted benzoyloxy, or each pair of substituents $R_2$ and $R_3$ or $R_3$ and $R_4$ or $R_4$ and $R_5$, together with the linking carbon atoms, forms a benzene ring, $R_4$ is additionally —$(CH_2)_p$—$COR_9$ or —$(CH_2)_q$OH, or, if $R_3$ and $R_5$ are hydrogen, $R_4$ is additionally a radical of formula II

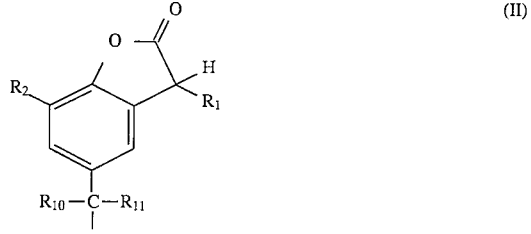

$R_8$ is hydrogen or $C_1$–$C_6$alkyl, $R_9$ is hydroxy, $C_1$–$C_{18}$alkoxy or

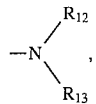

$R_{10}$ and $R_{11}$ are methyl groups or, together with the linking carbon atom, form a $C_5$–$C_8$-cycloalkylidene ring which is unsubstituted or substituted by 1 to 3 $C_1$–$C_4$alkyl groups;

$R_{12}$ and $R_{13}$ are each independently of the other hydrogen or $C_1$–$C_8$alkyl, and q is 2, 3, 4, 5 or 6.

A very particularly preferred process for the preparation of compounds of formula I is that wherein at least two of the substituents $R_2$, $R_3$, $R_4$ and $R_5$ are hydrogen.

Also very particularly preferred is a process for the preparation of compounds of formula I, wherein $R_3$ and $R_5$ are hydrogen.

A further very particularly preferred process for the preparation of compounds of formula I is that wherein $R_2$, $R_3$, $R_4$ and $R_5$ are each independently of one another hydrogen, chloro, hydroxy, $C_1$–$C_{18}$alkyl, $C_7$–$C_9$phenylalkyl, phenyl, $C_5$–$C_8$cycloalkyl, $C_1$–$C_6$alkoxy, cyclohexylcarbonyloxy or benzoyloxy, or each pair of substituents $R_2$ and $R_3$ or $R_3$ and $R_4$ or $R_4$ and $R_5$, together with the linking carbon atoms, forms a benzene ring, $R_4$ is additionally —$(CH_2)_p$—$COR_9$, or if $R_3$ and $R_5$ are hydrogen, $R_4$ is additionally a radical of formula II $R_9$ is hydroxy or $C_1$–$C_{18}$alkoxy, and $R_{10}$ and $R_{11}$ are methyl groups or, together with the linking carbon atom, form a $C_5$–$C_8$-cycloalkylidene ring.

A particularly interesting process for the preparation of compounds of formula I is that wherein $R_2$ is $C_1$–$C_{18}$alkyl or cyclohexyl, $R_3$ is hydrogen, $R_4$ is $C_1$–$C_4$alkyl, cyclohexyl or a radical of formula II, $R_5$ is hydrogen, and $R_{10}$ and $R_{11}$ together with the linking carbon atom, form a cyclohexylidene ring.

A further particularly interesting process for the preparation of compounds of formula I is that wherein $R'_{15}$ is hydrogen, $C_1$–$C_{18}$ alkanoyl, $C_3$–$C_{18}$alkenoyl, $C_3$–$C_{18}$ alkanoyl which is interrupted by oxygen, sulfur or >N—$_8$; $C_6$–$C_9$cycloalkylcarbonyl, thenoyl, furoyl, benzoyl or $C_1$–$C_8$-alkyl-substituted benzoyl; naphthoyl or $C_1$–$C_8$alkyl-substituted naphthoyl; $C_1$–$C_{18}$alkanesulfonyl, fluoro-substituted $C_1$–$C_{18}$ alkanesulfonyl; phenylsulfonyl or $C_1$–$C_8$alkyl-substituted phenylsulfonyl;

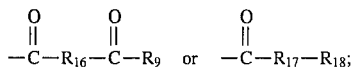

$R_{16}$ is a direct bond, $C_1$–$C_{12}$alkylene, $C_2$–$C_{12}$alkylene which is interrupted by oxygen, sulfur or >N—$R_8$; $C_2$–$C_{12}$alkenylene, $C_2$–$C_{12}$alkylidene, $C_7$–$C_{12}$phenylalkylidene, $C_5$–$C_8$cycloalkylene, $C_7$–$C_8$bicycloalkylene or phenylene, $R_{17}$ is oxygen or —NH—, and $R_{18}$ is $C_1$–$C_{12}$alkyl or phenyl.

A process of very special interest is that for the preparation of compounds of formula I, wherein $R_{15}$ is chloro, bromo or —$OR'_{15}$, $R'_{15}$ is hydrogen, $C_1$–$C_{12}$alkanoyl, $C_3$–$C_{12}$alkanoyl which is interrupted by oxygen; cyclohexylcarbonyl, benzoyl, naphthoyl, $C_1$–$C_{12}$alkanesulfonyl, fluoro-substituted $C_1$–$C_{12}$-alkanesulfonyl; phenylsulfonyl or $C_1$–$C_4$alkyl-substituted phenylsulfonyl; or

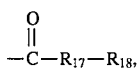

$R_{17}$ is —NH—, and $R_{18}$ is $C_1$–$C_8$alkyl or phenyl.

A process of very special interest is also that for the preparation of compounds of formula I, wherein $R_{15}$ is —$OR'_{15}$, $R'_{15}$ is hydrogen, $C_1$–$C_4$alkanoyl or

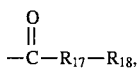

$R_{17}$ is —NH—, and $R_{18}$ is $C_1$–$C_4$alkyl.

Preferred reaction conditions of the inventive process are the following:

The reaction can be carried out at elevated temperature, preferably in the range from 70° to 200° C., in the melt or in a solvent and under normal pressure or slight vacuum.

It is particularly preferred to carry out the reaction in the boiling range of the compound of formula IV.

The preferred solvent is the compound of formula IV, which is simultaneously the reactant.

Suitable solvents are those which do not participate in the reaction, typically halogenated hydrocarbons, hydrocarbons, ethers or aromatic hydrocarbons.

Preferred halogenated hydrocarbons are dichloromethane, 1,2-dichloroethane, chloroform or carbon tetrachloride.

Preferred hydrocarbons are typically octane and the commercially available isomeric fractions such as the hexane faction, white spirit or ligroin.

Preferred ethers are typically dibutyl ether, methyl tert-butyl ether or diethylene glycol dimethyl ether.

Illustrative examples of deactivated aromatic hydrocarbons are nitrobenzene or pyridine.

When $R'_{15}$ is hydrogen in the compound of formula III (3-hydroxy-3H-benzofuran-2-one), the water of reation is conveniently removed continuously, preferably by adding an agent that absorbs water, for example a molecular sieve. Most preferably the water is removed continuously as an azeotrope by distillation via a water separator.

A process for the preparation of compounds of formula I, wherein the reaction is carried out in the presence of a catalyst, is also of interest.

Suitable catalysts are protonic acids, Lewis acids, aluminium silicates, ion exchange resins, zeolites, naturally occurring sheet silicates or modified sheet silicates.

Illustrative examples of suitable protonic acids are acids of inorganic or organic salts, typically hydrochloric acid, sulfuric acid, phosphoric acid, methanesulfonic acid, p-toluenesulfonic acid, or carboxylic acids such as acetic acid. p-Toluenesulfonic acid is particularly preferred.

Illustrative examples of suitable Lewis acids are tin tetrachloride, aluminium chloride, zinc chloride or borotrifluoride etherate. Tin tetrachloride and aluminium chloride are especially preferred.

Illustrative examples of suitable aluminium silicates are those that are widely used in the petrochemical industry and are also known as amorphous aluminium silicates. These compounds contain c. 10–30% of silicon monoxide and 70–90% of aluminium oxide. A particularly preferred aluminium silicate is HA-HPV® available from Ketjen (Akzo).

Illustrative examples of suitable ion exchange resins are styrene-divinylbenzene resins which additionally carry sulfonic acid groups, for example Amberlite® and Amberlyst® available from Rohm and Haas, or Dowex 50® available from Dow Chemicals; perfluorinated ion exchange resins such as Nafion H® sold by DuPont; or other superacid ion exchange resins such as those as described by T. Yamaguchi, Applied Catalysis, 61, 1–25 (1990) or M. Hino et al., J. Chem. Soc. Chem. Commun. 1980, 851–852.

Suitable zeolites are typically those widely used in petrochemistry as cracking catalysts and known as crystalline silicon-aluminium oxides of different crystal structure. Particularly preferred zeolites are the Faujasites available from Union Carbide, for example Zeolith X®, Zeolith Y® and ultrastable Zeolith Y®; Zeolith Beta® and Zeolith ZSM-12® available from Mobil Oil Co.; and Zeolith Mordenit® available from Norton.

Suitable naturally occurring sheet silicates are termed "acid clays" and typically include bentonites or montmorillonites, which are degraded, ground, treated with mineral acids and calcined industrially. Particularly suitable naturally occurring sheet silicates are the Fulcat® types available from Laporte Adsorbents Co., for example Fulcat 22A®, Fulcat 22B®, Fulcat 20®, Fulcat 30® or Fulcat 40®; or the Fulmont® types available from Laporte Adsobents Co., for example Fulmont XMP-3® or Fulmont XMP-4®. A particularly preferred catalyst is Fulcat 22B®. The other Fulcat® types and Fulmont® types also belong to this preferred class, because there are only minor differences between the individual types, as for example in the number of acid centres.

Modified sheet silicates are also termed "pillared clays" and are derived from the above described naturally occurring sheet silicates by additionally containing between the silicate layers oxides of e.g. zirconium, iron, zinc, nickel, chromium, cobalt or magnesium. This type of catalyst is widely used, as described in the literature, inter alia by J. Clark et al., J. Chem. Soc. Chem. Commun. 1989, 1353–1354, but is available from only a very few firms. Particularly preferred modified sheet silicates typically include Envirocat EPZ-10®, Envirocat EPZG® or Envirocat EPIC® available from Contract Chemicals.

A particularly preferred process for the preparation of compounds of formula I is also that wherein the reaction is carried out in the presence of a catalyst which is a naturally occurring sheet siliate or a modified sheet silicate.

Also especially preferred is a process for the preparation of compounds of formula I, wherein the reaction is carried out in the presence of a catalyst of the Fulcat® type.

The catalyst is conveniently added in an amount of 1 to 60% by weight and, if a particularly preferred catalyst of the Fulcat® type is used, in an amount of 1 to 30% by weight, with respect to the compound of formula III.

A particularly interesting process is that for the preparation of compounds of formula I, wherein, when n is 1, the molar ratio of the compound of formula III to the compound of formula IV is 1:1 to 1:20, and, when n is 2, the molar ratio of the compound of formula III to the compound of formula IV is 3:1 to 2:1.

In the process of this invention, compounds of formula IV, which also yield mixtures of isomers in other known electrophilic substitution reactions, likewise give compounds of formula I in the form of mixtures of isomers. The relative distribution of the isomers will depend on the commonly known basic rules of organic chemistry for electrophilic aromatic substitution reactions.

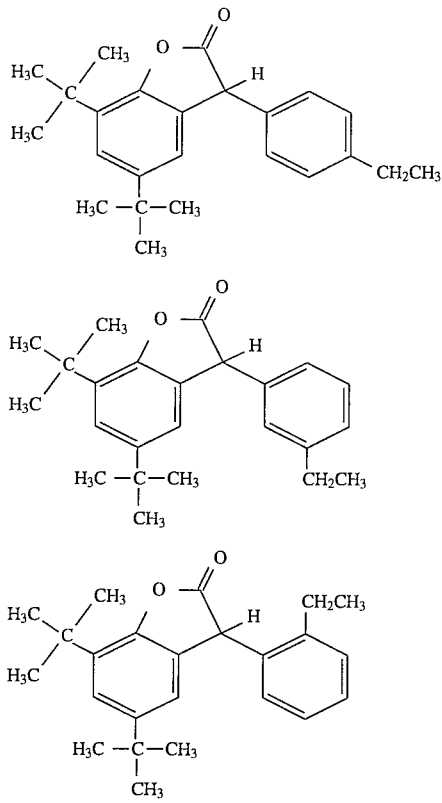

As described in Example 4, reaction of e.g. 5,7-di-tert-butyl-3-hydroxy-3H-benzofuran-2-one (compound (201), Table 2) with ethyl benzene, using Fulcat 22B as catalyst, gives 59.2% of the para-isomer (compound (105), Table 1), 10.8% of the meta-isomer (compound (105A) and 21.1% of the ortho-isomer (compound (105B).

The isomers can be purified and separated by fractional crystallisation or chromatography on e.g. silica gel. It is preferred to use the mixtures of isomers as stabilisers for organic materials.

The compounds of formula IV are novel and some are commercially available or can be prepared by per se known methods.

Some of the compounds of formula III, wherein $R'_{15}$ is hydrogen, can be obtained in their tautomeric forms of formula IIIa or formula IIIb

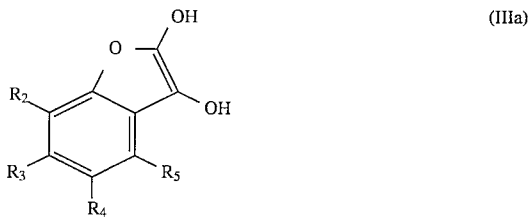

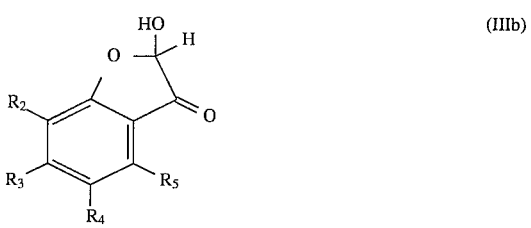

as described by H. Sterk et at., Monatshefte für Chemie 99, 2223 (1968). Within the scope of this application, formula III is always to be understood as also embracing the two tautomeric formulae IIIa and IIIb.

The compounds of formula III can be prepared by methods analogous to literature methods described at the outset. Preferred, however, is a novel process that is the subject matter of a parallel patent application, which comprises reacting a) one equivalent of a phenol of formula VII

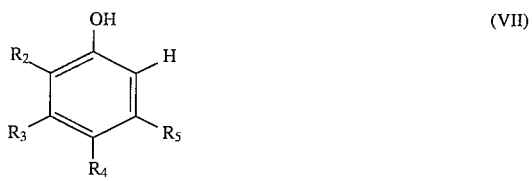

wherein the general symbols are as defined for formula I, with 0.8 to 2.0 equivalents, preferably with 0.8 to 1.2 equivalents, of glyoxylic acid, to a compound of formula VIII

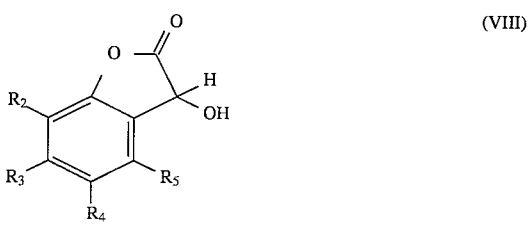

wherein the general symbols are as defined for formula I, and b) to prepare compounds of formula I, wherein $R'_{15}$ is not hydrogen, reacting the resultant compound of formula VIII with a hydrohalic acid, a halide of an oxysulfuric acid, a halide of phosphoric acid, a halide of phosphorous acid, with an acid of formula IX

$$R'_{15}—OH \qquad (IX)$$

an acid halide of formula X

$$R'_{15}—Y \qquad (X)$$

an ester of formula XI

$$R'_{15}—O—R_{38} \qquad (XI)$$

a symmetrical or unsymmetrical anhydride of formula XII

$R'_{15}$—O—$R'_{15}$ (XII)

or an isocyanate of formula XIII

$R_{39}$—N=C=O (IX)

wherein $R'_{15}$ is as defined above, with the proviso that $R'_{15}$ in the compounds of formulae IX, X, XI and XII is not hydrogen;

$R_{38}$ is $C_1$-$C_8$alkyl, $R_{39}$ is $C_1$-$C_{18}$alkyl or phenyl, and

Y is fluoro, chloro, bromo or iodo.

The glyoxylic acid can be used either in crystalline form or, conveniently, in the form of a commercial aqueous solution, usually a 40 to 60% aqueous solution.

A particularly interesting process for the preparation of compounds of formula VIII therefore comprises using the glyoxylic acid in the form of a 40 to 60% aqueous solution, preferably of 50% aqueous glyoxylic acid.

The water present in the glyoxylic acid and the water of reaction is removed by distillation during the reaction, conveniently using a solvent that forms an azeotropic mixture with water.

Suitable solvents that form an azeotropic mixture with water do not participate in the reaction and typically include hydrocarbons such as cyclohexane or methyl cyclohexane; aromatic hydrocarbons such as benzene or toluene; halogenated hydrocarbons such as 1,2-dichloroethane; or ethers such as methyl tert-butyl ether.

When carrying out the reaction of the phenol of formula VII with glyoxylic acid without a solvent to give the compounds of formula VIII in the melt, the water of reaction is conveniently distilled off under normal pressure, preferably under a slight vacuum.

It is preferred to carry out the reaction at elevated temperature, preferably in the range from 60° to 120° C. A particularly preferred temperature range is from 60° to 90° C.

The reaction can be catalysed by the addition of a minor amount of a protonic acid such as p-toluenesulfonic acid, methanesulfonic acid, sulfuric acid or hydrochloric acid; or of a Lewis acid such as borotrifluoride etherate or aluminium chloride.

The amount of catalyst is 0.01 to 5 mol %, preferably 0.1 to 1.0 mol %, based on the phenol of formula VII.

The reaction conditions for process step b) for the preparation of compounds of formula III, wherein $R'_{15}$ is not hydrogen, starting from compounds of formula VIII, are commonly known and can be chosen, inter alia, in analogy to esterification procedures described in Organikum 1986, pages 186–191, page 388 and pages 402–408.

Suitable hydrohalic acids are typically hydrochloric acid, hydrobromic acid or hydriodic acid. Hydrochloric acid is preferred.

Suitable halides of an oxysulfuric acid are typically thionyl chloride, sulfuryl chloride or thionyl bromide. Thionyl chloride is preferred.

Suitable halides of phosphoric acid and phosphorous acid typically include phosphorus trichloride, phosphorus tribromide, phosphorus triiodide, phosphorus pentachloride, phosphoroxy chloride or phosphorus pentafluoride. Phosphoroxy chloride is particularly preferred.

In process step b) it is preferred to use a halide of an oxysulfuric acid such as thionyl chloride; an acid halide of formula X; an ester of formula XI; or a symmetrical anhydride of formula XII.

When using a halide of an oxysulfuric acid such as thionyl chloride in process step b), it is preferred to carry out the reaction of a compound of formula VIII without a solvent and in the temperature range from 0° to 40° C., preferably at room temperature. The thionyl chloride is conveniently used in a 2- to 10-fold excess, preferably in a 2- to 6-fold excess, with respect to the compound of formula VIII. The reaction can also be carried out in the presence of a catalyst such as dimethyl formamide.

When using an acid of formula IX ($R'_{15}$—OH) in process step b), the reaction is preferably carried out in the presence of an inert organic solvent such as dichloromethane, dioxane, diethyl ether or tetrahydrofuran, and in the presence of a reagent that binds water physically or chemically, conveniently a molecular sieve or dicyclohexylcarbodiimide.

If an acid halide of formula X ($R'_{15}$—Y), wherein Y is preferably chloro or bromo, most preferably chloro, is used in process step b), it is preferred to carry out the reaction of the compound of formula VIII in the presence of a solvent and a base. The base can be used in varying amounts, from catalytic through stochiometric mounts to the multiple molar excess with respect to the compound of formula VIII. The hydrogen chloride formed during the reaction may be converted by the base into the chloride, which can be removed by filtration and/or washing with a suitable aqueous or solid phase, in which case a second water-immiscible solvent can also be used. The product is conveniently purified by recrystallising the residue of the organic phase, which is concentrated or evaporated to dryness.

Suitable solvents for carrying out the reaction include hydrocarbons (typically toluene, xylene, hexane, pentane or further petroleum ether fractions), halogenated hydrocarbons (typically di- or trichloromethane, 1,2-dichloroethan, 1,1,1-trichloroethane), ethers (e.g. diethyl ether, dibutyl ether or tetrahydrofuran), and also acetonitrile, dimethyl formamide, dimethyl sulfoxide, N-methylpyrrolidone.

Suitable bases include tertiary amines, e.g. trimethylamine, triethylamine, tributylamine, N,N-dimethylaniline, N,N-diethylaniline; pyridines; hydrides (e.g. lithium, sodium or potassium hydride) or alcoholates (e.g. sodium methylate).

If an ester of formula XI ($R'_{15}$—O—$R_{38}$), wherein $R_{38}$ is preferably $C_1$-$C_4$alkyl, most preferably methyl or ethyl, is used in process step b), it is preferred to carry out the reaction of the compound of formula VIII in the presence of a solvent that forms an azeotropic mixture with alcohols. The alcohol ($R_{38}$—OH) that forms during the reaction can be removed continuously by distillation.

Suitable solvents that form an azeotropic mixture with alcohols do not participate in the reaction and typically include hydrocarbons such as cyclohexane; aromatic hydrocarbons such as benzene or toluene; halogenated hydrocarbons such as 1,2-dichloroethane; or ethers such as methyl tert-butyl ether.

The reaction can be catalysed with a minor amount of a protonic acid such as p-toluenesulfonic acid, methanesulfonic acid, sulfuric acid or hydrochloric acid; as well as of a Lewis acid such as borotrifluoride etherate or aluminium chloride.

If a symmetrical anhydride of formula XII ($R'_{15}$—O—$R'_{15}$) wherein $R'_{15}$ is preferably $C_2$-$C_6$alkanoyl, preferably acetyl, is used in process step b), it is preferred to carry out the reaction with a compound of formula VIII without the addition of a further solvent and in the temperature range from 20° to 200° C., e.g. the boiling temperature of the anhydride of formula XII, preferably from 60° to 180° C.

If an isocyanate of formula XIII ($R_{39}$—N=C=O) is used, it is preferred to carry out the reaction with a compound of formula VIII without the addition of a further solvent and in the temperature range from 20° to 200° C., e.g. the boiling temperature of the isocyanate of formula XIII, preferably from 60° to 180° C.

The reaction with an isocyanate is likewise preferably carried out in the presence of a catalyst. Preferred catalysts correspond to those referred to above previously in connection with the reaction of the compound of formula III with a compound of formula IV.

The phenols of formula VII are known or can be prepared by per se known processes.

Bisphenols of formula XIV

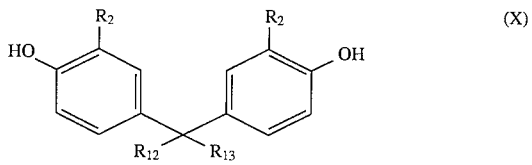

can be prepared in accordance with Houben-Weyl, Methoden der organischen Chemie, Vol. 6/1c, 1030.

The compounds of formula I can also be prepared by a so-called one-pot process starting from the phenols of formula VII.

Accordingly, the invention also relates to a process for the preparation of compounds of formula I

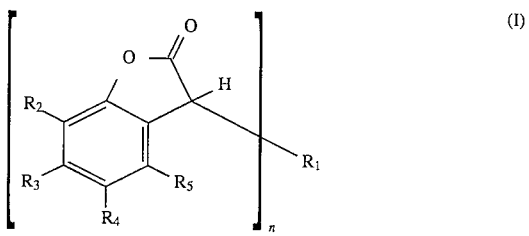

which comprises reacting one equivalent of the phenol of formula VII

with 0.8 to 2.0 equivalents of glyoxylic acid to a compound of formula VIII

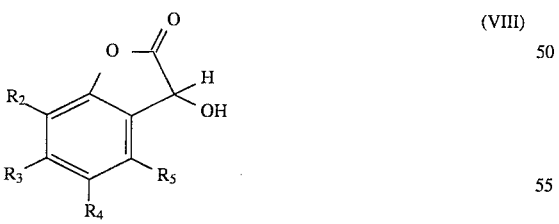

and subsequently reacting said compound of formula VIII, without isolation, with a compound of formula IV

[H]$_n$—R$_1$ (IV).

The definitions of the general symbols in connection with the inventive one-pot process are the same as for the inventive processes discussed previously.

The preferred reaction parameters for the one-pot process correspond to those previously discussed in detail in connection with the two single steps.

Prior to the further reaction with a compound of formula IV, the 3-hydroxy-3H-benzofuran-2-ones of formula VIII initially formed in the one-pot process can be subjected to an additional reaction step by substituting the hydroxyl group with halogen or activating it with a leaving group.

Accordingly, the invention also relates to a one-pot process for the preparation of compounds of formula I, which comprises reacting one equivalent of the phenol of formula VII with 0.8 to 2.0 equivalents of glyoxylic acid to the 3-hydroxy-3H-benzofuran-2-one of formula VIII which, without isolation before the further reaction with a compound of formula IV, is reacted in an additional reaction step with a hydrohalic acid, a halide of an oxysulfuric acid, a halide of phosphoric acid, a halide of a phosphorous acid, an acid of formula IX

R'$_{15}$—OH (IX)

an acid halide of formula X,

R'$_{15}$—Y (X)

an ester of formula XI

R'$_{15}$—O—R$_{38}$ (XI)

a symmetrical or unsymmetrical anhydride of formula XII

R'$_{15}$—O—R'$_5$ (XII)

or an isocyanate of formula XIII

R$_{39}$—N=C=O (XIII)

wherein

R'$_{15}$ in formulae IX, X, XI and XII is not hydrogen;

R$_{38}$ is C$_1$–C$_8$alkyl,

R$_{39}$ is C$_1$–C$_{18}$alkyl or phenyl, and

Y is fluoro, chloro, bromo or iodo, to a compound of formula III

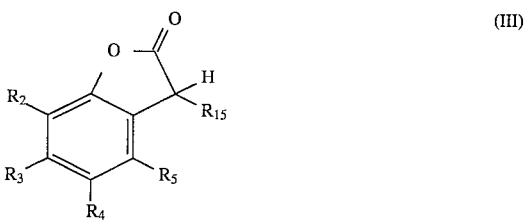

wherein, when R$_{15}$=—OR'$_{15}$, R'$_{15}$ is not hydrogen.

The preferred reaction parameters for this additional reaction step correspond to those previously described in detail in connection with the preparation of the compounds of formula III starting from compounds of formula VIII.

A particularly preferred one-pot process for the preparation of compounds of formula I comprises using a compound of formula VII that differs from the compound of formula IV.

The invention is illustrated in more detail by the following Examples, in which parts and percentages are by weight.

EXAMPLE 1

Process for the preparation of 5,7-di-tert-butyl-3-(2,5-dimethylphenyl)-3H-benzofuran-2-one (compound (101), Table 1) starting from 5,7-di-tert-butyl-3-hydroxy-3H-benzofuran-2-one (compound (201), Table 2) with p-xylene, as well as Fulcat 22B as catalyst.

a) Preparation of 5,7-di-tert-butyl-3-hydroxy-3H-benzofuran-2-one (compound (201), Table 2).

A mixture of 212.5 g (1.00 mol) of 2,4-di-tert-butylphenol (97%), 163.0 g (1.10 mol) of 50% aqueous glyoxylic acid and 0.5 g (2.6 mmol) of p-toluenesulfonic acid monohydrate in 300 ml of 1,2-dichloroethane is refluxed under nitrogen for 3.5 hours on a water separator. Afterwards the reaction mixture is concentrated on a vacuum rotary evaporator. The residue is taken up in 800 ml of hexane and washed three times with water. The aqueous phases are separated in the separating funnel and further extracted with 300 ml of hexane. The organic phases are combined, dried over magnesium sulfate and concentrated on a vacuum rotary evaporator. The residue yields 262.3 g (~100%) of analytically pure 5,7-di-tert-butyl-3-hydroxy-3H-benzofuran-2-one in the form of a thick yellowish resin (compound (201), Table 2).

In analogy to Example 1a, compounds (202), (203), (204), (205), (209), (210) and (211) are prepared from the corresponding phenols such as 2-tert-butyl-4-methylphenol, 4-tert-butyl-2-methylphenol, 2,4-dicyclohexylphenol, 2-(hexadec-2-yl)-4-methylphenol, 3-[3-tert-butyl-4-hydroxyphenyl]propionic acid, 2,4-bis($\alpha,\alpha$-dimethylbenzyl)phenol and 4-methyl-2-(1,1,3,3-tetramethylbut-1-yl)phenol with glyoxylic acid. To prepare compound (207), 2 equivalents of glyoxylic acid are used starting from 1,1-bis(3-tert-butyl-4-hydroxyphenyl)cyclohexane.

b) Preparation of 5,7-di-tert-butyl-3-(2,5-dimethylphenyl)-3H-benzofuran-2-one (compound (101), Table 1)

To a solution of 262.3 g (1.00 mol) of 5,7-di-tert-butyl-3-hydroxy-3H-benzofuran-2-one (compound (201), Table 2, Example 1a) in 500 ml (4.05 mol) of p-xylene are added 40 g of Fulcat 22B and the mixture is refluxed for 1.5 hours on a water separator. The Fulcat 22B catalyst is then removed by filtration and excess p-xylene is removed by distillation on a vacuum rotary evaporator. Crystallisation of the residue from 400 ml of methanol yields 280.6 g (80%) of 5,7-di-tert-butyl-3-(2,5-dimethylphenyl)-3H-benzofuran-2one, m.p. 93°–97° C. (compound (101), Table 1).

EXAMPLE 2

Process for the preparation of 5,7-di-tert-butyl-3-(2,5-dimethylphenyl)-3H-benzofuran-2-one (compound (106), Table 1) starting from 3-acetoxy-5,7-di-tert-butyl-3H-benzofuran-2-one (compound (206), Table 2) with p-xylene, as well as Fulcat 22B as catalyst.

a) Preparation of 3-acetoxy-5,7-di-tert-butyl-3H-benzofuran-2-one (compound (206), Table 2).

A mixture of 21.2 g (0.10 mol) of 2,4-di-tert-butylphenol (97%), 16.3 g (0.11 mol) of 50% aqueous glyoxylic acid and 0.05 g (0.26 mmol) of p-toluenesulfonic acid monohydrate in 30 ml of 1,2-dichloroethane is refluxed under nitrogen for 3.5 hours on a water separator. Afterwards the reaction mixture is concentrated on a vacuum rotary evaporator. The residue is taken up in 9.9 ml (0.105 mol) of acetic anhydride and the solution is refluxed for 90 minutes. The reaction mixture is then cooled to room temperature, diluted with 100 ml of tert-butyl methyl ether and washed in succession with water and dilute sodium hydrogencarbonate solution. The aqueous phases are separated and extracted with 50 ml of tert-butyl methyl ether. The organic phases are combined, dried over magnesium sulfate and concentrated on a vacuum rotary evaporator. Chromatography of the residue on silica gel with the solvent system dichloromethane/hexane=2:1 yields 28.0 g (92%) of 3-acetoxy-5,7-di-tert-butyl-3H-benzofuran-2-one (compound (206), Table 2) as a thick reddish resin.

b) Preparation of 5,7-di-tert-butyl-3-(2,5-dimethylphenyl)-3H-benzofuran-2-one (compound (101), Table 1)

To a solution of 15.3 g (50.0 mmol) of 3-acetoxy-5,7-di-tert-butyl-3H-benzofuran-2-one (compound (206), Table 2, Example 2a) in 25 ml (0.20 mol) of p-xylene is added 1.0 g of Fulcat 22B and the mixture is refluxed for 17 hours on a water separator. The Fulcat 22B catalyst is then removed by filtration and excess p-xylene is removed by distillation on a vacuum rotary evaporator. Crystallisation of the residue from 20 ml of methanol yields 10.5 g (60%) of 5,7-di-tert-butyl-3-(2,5-dimethylphenyl)-3H-benzofuran-2-one, m.p. 93°–97° C. (compound (101), Table 1).

EXAMPLE 3

Process for the preparation of 3-(3,4-dimethylphenyl)-5,7-di-tert-butyl-3H-benzofuran-2-one (compound (103), Table 1) starting from 5,7-di-tert-butyl-3-hydroxy-3H-benzofuran-2-one (compound (201), Table 2) with o-xylene, as well as Fulcat 22B as catalyst.

To a solution of 262.3 g (1.00 mol) of 5,7-di-tert-butyl-3-hydroxy-3H-benzofuran-2-one (compound (201), Table 2, Example 1a) in 500 ml (4.05 mol) of o-xylene are added 40 g of Fulcat 22B and the mixture is refluxed for 1.5 hours on a water separator. The Fulcat 22B catalyst is then removed by filtration and excess p-xylene is removed by distillation on a vacuum rotaray evaporator. Crystallisation of the residue from 500 ml of methanol yields 244 g (69%) of 3-(3,4-dimethylphenyl)-5,7-di-tert-butyl-3H-benzofuran-2-one, m.p. 130°–132° C. (compound (103), Table 1), which additionally contains c. 1.3% of the structural isomer [3-(2, 3-dimethylphenyl)-5,7-di-tert-butyl-3H-benzofuran-2-one, compound (103A)]. The mother liquor yields a further 42.4 g of product which, according to GC-MS analysis, consists of 12.3% of the compound (103) and 87.7% of the isomeric compound (103A).

EXAMPLE 4

Process for the preparation of 5,7-di-tert-butyl-3-(4-ethylphenyl)-3H-benzofuran-2-one (compound (105), Table 1) starting from 5,7-di-tert-butyl-3-hydroxy-3H-benzofuran-2-one (compound (201), Table 2), with ethyl benzene, as well as Fulcat 22B as catalyst.

To a solution of 262.3 g (1.00 mol) of 5,7-di-tert-butyl-3-hydroxy-3H-benzofuran-2-one (compound (201), Table 2, Example 1a) in 500 ml (4.08 mol) of ethyl benzene are added 40 g of Fulcat 22B and the mixture is refluxed for 1.5 hours on a water separator. The Fulcat 22B catalyst is then removed by filtration and excess ethyl benzene is removed by distillation on a vacuum rotaray evaporator. GC-MS analysis shows the residue to consist of a mixture of 59.2% of the para-isomer (compound (105), Table 1), 10.8% of the meta-isomer (compound (105A) and 21.1% of the ortho-isomer(compound (105B). Crystallisation of the residue from 400 ml of methanol yields 163.8 g (47%) of 5,7-di-tert-butyl)-3-(4-ethylphenyl)-3H-benzofuran-2-one (compound (105), Table 1) (para-isomer), which additionally contains 5.6% of the meta-isomer 5,7-di-tert-butyl-3-(3-ethylphenyl)-3H-benzofuran-2-one (compound (105A) and 1.3% of the ortho-isomer 5,7-di-tert-butyl-3-(2-ethylphenyl)3H-benzofuran-2-one (compound (105B ). Further crystallisation from methanol yields the almost pure para-isomer (compound (105), Table 1), m.p. 127°–132° C.

In accordance with the general procedure described in this Example, compounds (102), (106), (107), (116), (117), (118), (120), (122), (123), (124), (125), (126) and (127) are prepared from 5,7-di-tert-butyl-3-hydroxy-3H-benzofuran-2-one (compound (201), Table 2, Example 1a) and the corresponding aromatic hydrocarbons, typically including m-xylene, isopropylbenzene(cumene), tert-butylbenzene, 2,6-dimethylanisole, anisole, acetoxyethoxybenzene, chlorobenzene, biphenyl, thiophene, p-xylene, dibenzofuran, phenanthren and diphenyl ether. To prepare compound (127), 2 equivalents of 5,7-di-tert-butyl-3-hydroxy-3H-benzofuran-2-one are used starting from diphenyl ether.

EXAMPLE 5

Process for the preparation of 5,7-di-tert-butyl-3-(2,3,4,5,6-pentamethylphenyl)-3H-benzofuran-2-one (compound (111), Table 1) starting from 5,7-di-tert-butyl-3-hydroxy-3H-benzofuran-2-one (compound (201), Table 2) with pentamethylbenzene, as well as tin tetrachloride as catalyst.

11.5 g (77.5 mmol) of pentamethylbenzene and 10 ml (85.0 mmol) of tin tetrachloride are added to a solution of 19.7 g (75.0 mmol) of 5,7-di-tert-butyl-3-hydroxy-3H-benzofuran-2-one (compound (201), Table 2, Example 1a) in 50 ml of 1,2-dichloroethane and the reaction mixture is refluxed for 1hour. The reaction mixture is diluted with water and extracted 3 times with toluene. The organic phases are combined, washed with water, dried over sodium sulfate and concentrated on a vacuum rotary evaporator. Crystallisation of the residue from ethanol yields 26.3 g (89%) of 5,7-di-tert-butyl-3-(2,3,4,5,6-pentamethylphenyl)-3H-benzofuran-2-one, m.p. 185°–190° C. (compound (111), Table 1).

In accordance with the general procedure of this Example, compounds (109) and (110) are prepared from 5,7-di-tert-butyl-3-hydroxy-3H-benzofuran-2-one (compound (201), Table 2, Example 1a) and the corresponding aromatic hydrocarbons, for example n-dodecylbenzene and 1,2,3-trimethylbenzene.

EXAMPLE 6

Process for the preparation of 5,7-di-tert-butyl-3-phenyl-3H-benzofuran-2-one (compound (108), Table 1) starting from 5,7-di-tert-butyl-3-hydroxy-3H-benzofuran-2-one (compound (201), Table 2) with benzene, as well as aluminium trichloride as catalyst.

73.3 g (0.55 mol) of ground aluminium trichloride are added over 25 minutes to a solution of 131.2 g (0.50 mol) of 5,7-di-tert-butyl-3-hydroxy-3H-benzofuran-2-one (compound (201), Table 2, Example 1a) in 250 ml (2.82 mol) of benzene and the reaction mixture is heated for 1.5 hours to reflux temperature and then refluxed for 1.5 hours. The reaction mixture is cooled to room temperature and then, cautiously with cooling, 200 ml of water are added, followed by the addition of concentrated hydrochloric acid until a homogeneous two-phase mixture forms. The organic phase is separated, washed with water, dried over sodium sulfate and concentrated on a vacuum rotary evaporator. Crystallisation of the residue from ethanol yields 97.8 g (64%) of 5,7-di-tert-butyl-3-phenyl-3H-benzofuran-2-one, m.p. 116°–119° C. (compound (108), Table 1).

In accordance with the procedure of this Example, compounds (113), (114) and (119) are prepared from the corresponding 3-hydroxy-3H-benzofuran-2-ones such as 7-[2-(hexadec-2-yl)]-3-hydroxy-5-methyl-3H-benzofuran-2-one (compound (205), Table 2), 5,7-dicyclohexyl-3-hydroxy-3H-benzofuran-2-one (compound (204), Table 2) and 5,7-di-tert-butyl-3-hydroxy-3H-benzofuran-2-one (compound (201), Table 2) and the corresponding aromatic hydrocarbons such as benzene and thioanisole.

EXAMPLE 7

Process for the preparation of 5,7-di-tert-butyl-3-(4-methylphenyl)-3H-benzofuran-2-one (compound (104), Table 1) starting from 2,4-di-tert-butylphenol, without isolation of 5,7-di-tert-butyl-3-hydroxy-3H-benzofuran-2-one (compound (201), Table 2), with glyoxylic acid and toluene, as well as Fulcat 22B as catalyst.

A mixture of 21.2 g (0.10 mol) of 2,4-di-tert-butylphenol (97%), 16.3 g (0.11 mol) of 50% aqueous glyoxylic acid, 2.0 g of Fulcat 22B and 50 ml of toluene is refluxed for 8 hours under nitrogen on a water separator. The Fulcat 22B catalyst is then removed by filtration and excess toluene is distilled off on a vacuum rotary evaporator. Crystallisation of the residue from 40 ml of ethanol yields 14.2 g (42%) of 5,7-di-tert-butyl-3-(4-methylphenyl)-3H-benzofuran-2-one, m.p. 130°–133° C. (compound (104), Table 1).

In accordance with the general procedure of this Example, compound (112) is prepared starting from 2-tert-butyl-4-methylphenol instead of from 2,4-di-tert-butylphenol.

EXAMPLE 8

Process for the preparation of 4,4'-bis(5,7-di-tert-butyl-3H-benzofuran-2-on-3-yl)-N-methyl-diphenylamine (compound (121), Table 1) starting from 5,7-di-tert-butyl-3-hydroxy-3H-benzofuran-2-one (compound (201), Table 2), with N-methyl-diphenylamine, as well as p-toluenesulfonic acid as catalyst.

30.2 g (115.0 mmol) of 5,7-di-tert-butyl-3-hydroxy-3H-benzofuran-2-one (compound (201), Table 2, Example 1a) are added over 2 hours to a boiling solution of 9.20 g (50.0 mmol) of N-methyl-diphenylamine and 0.20 g of p-toluenesulfonic acid monohydrate in 50 ml of ligroin (mixture of alkanes with a boiling range of 140°–160° C.). The reaction mixture is then refluxed for 4 hours on a water separator, then cooled and concentrated on a vacuum rotary evaporator. Crystallisation of the residue from isopropanol/water=9:1 yields 18.9 g (56%) of 4,4'-bis(5,7-di-tert-butyl-3H-benzofuran-2-on-3-yl)-N-methyl-diphenylamine, m.p. 135°–145° C. (compound (121), Table 1).

EXAMPLE 9

Process for the preparation of 5,7-di-tert-butyl-3-(3,5-dimethyl-4-hydroxyphenyl)-3H-benzofuran-2-one (compound (115), Table 1) starting from 5,7-di-tert-butyl-3-hydroxy-3H-benzofuran-2-one (compound (201), Table 2) with 2,6-dimethylphenol, as well as p-toluenesulfonic acid as catalyst.

30.2 g (115.0 mmol) of 5,7-di-tert-butyl-3-hydroxy-3H-benzofuran-2-one (compound (201), Table 2, Example 1a) are added over 2 hours to a boiling solution of 12.2 g (100.0 mmol) of 2,6-dimethylphenol and 0.20 g of p-toluenesulfonic acid monohydrate in 50 ml of acetic acid. The reaction mixture is then refluxed for 4 hours, cooled, and concentrated on a vacuum rotary evaporator. Two crystallisations of the residue from isopropanol/water= 9:1 yield 28.5 g (78%) of 5,7-di-tert-butyl-3-(3,5-dimethyl-4-hydroxyphenyl)-3H-benzofuran-2-one, m.p. 225°–228° C. (compound (115), Table 1).

EXAMPLE 10

Process for the preparation of 7-tert-butyl-5-methyl-3-(9-methyl-9H-carbazol-3-yl)-3H-benzofuran-2-one (compound (128), Table 1) starting from 7-tert-butyl-3-hydroxy-5-methyl-3H-benzofuran-2-one (compound (202), Table 2) with N-methylcarbazole and n-octane, as well as Fulcat 22B as catalyst.

A mixture of 2.2 g (10.0 mmol) of 7-tert-butyl-3-hydroxy-5-methyl-3H-benzofuran-2-one (compound (202), Example 1a, Table 2), 1.8 g (10.0 mmol) of N-methylcarbazole and 0.2 g of Fulcat 22B and 20 ml of n-octane is refluxed for 5 hours under nitrogen. The Fulcat 22B catalyst is subsequently removed by filtration and excess n-octane is distilled off on a vacuum rotary evaporator. Chromatography of the residue on silica gel with the solvent system dichloromethane/hexane=1:2 to 1:1 and subsequent crystallisation of the pure fractions from methanol yields 0.70 g (10%) of 7-tert-butyl-5-methyl-3-(9-methyl-9H-carbazol-3-yl)-3H-benzofuran-2-one, m.p. 84°–90° C. (compound (128), Table 1). The product may additionally contain minor amounts of other structural isomers in accordance with the substitution at the carbazole ring.

EXAMPLE 11

Process for the preparation of 5,7-di-tert-butyl-3-(9H-fluoren-3-yl)-3H-benzofuran-2-one (compound (129), Table 1) starting from 2,4-di-tert-butylphenol, without isolation of 5,7-di-tert-butyl-3-hydroxy-3H-benzofuran-2-one (compound (201), Table 2), with glyoxylic acid and fluorene, as well as p-toluenesulfonic acid and Fulcat 22B as catalyst.

A mixture of 15.9 g (75 mmol) of 2,4-di-tert-butylphenol (97%), 12.2 g (82 mmol) of 50% aqueous glyoxylic acid, 40 mg (0.20 mmol) of p-toluenesulfonic acid monohydrate and 25 ml of 1,2-dichloroethane is refluxed for 3.5 hours under nitrogen on a water separator. The reaction mixture is thereafter concentrated on a vacuum rotary evaporator. The residue is dissolved in 30 ml of n-octane and 12.5 g (75 mmol) of fluorene and 3 g of Fulcat 22B are added to the solution. This reaction mixture is refluxed for 3.5 hours under nitrogen on a water separator, then cooled and filtered. The filtrate is concentrated on a vacuum rotary evaporator. Chromatography of the residue on silica gel with the solvent system dichloromethane/hexane=2:1 and subsequent crystallisation of the pure fractions from methanol yields 5.28 g (17%) of 5,7-di-tert-butyl-3-(9H-fluoren-3-yl)-3H-benzofuran-2-one, m.p. 140°–153° C. (compound (129), Table 1). The product may additionally contain minor amounts of other structural isomers in accordance with the substitution at the fluorene ring.

EXAMPLE 12

Process for the preparation of a c. 5.7:1 mixture of 3-(3,4-dimethylphenyl)-5,7-di-tert-butyl-3H-benzofuran-2-one (compound (103), Table 1 and 3-(2,3-dimethylphenyl)-5,7-di-tert-butyl-3H-benzofuran-2-one (compound (103A)) isomers starting from 2,4-di-tert-butylphenol with glyoxylic acid and o-xylene, as well as Fulcat or Fulmont as catalyst.

To a 1.5 l double-walled reactor with water separator are charged 206.3 g (1.0 mol) of 2,4-di-tert-butylphenol, 485 g (5.5 mol) of o-xylene, 0.5 g (2.6 mol) of p-toluenesulfonic acid monohydrate and 163 g (1.1 mol) of 50% aqueous glyoxylic acid. With stirring, the mixture is heated to 85°–90° C. and the apparatus is simultaneously evacuated to c.450 mbar. As soon as the temperature in the reactor is 85°–90° C., a mixture of o-xylene/water begins to distill from the mixture, the o-xylene being refluxed and the water removed from the system. The vacuum is then raised continuously so that the temperature in the reactor can be kept at 85°–90° C. Altogether c. 98–100 ml of water are distilled over 3 to 4 hours. The vacuum is then released with nitrogen and 40 g of catalyst (Fulcat 30 or 40, Fulmont XMP-3 or XMP-4) are added to the clear yellow solution. The apparatus is evacuated to a pressure of 700 mbar and the suspension is stirred at a heating bath temperature of 165° C. The water of reaction begins to distill from the system as an azeotrope from a temperature of c. 128° C. The temperature in the apparatus rises towards the end to a maximum of 140° C. A total amount of c. 20 ml of water distills from the system over 1 to 2 hours. The vacuum is then released with nitrogen. The reaction mixture is cooled to 90°–100° C. and filtered. The apparatus and the filter residue are rinsed with 100 g of o-xylene. The filtrate is transferred to a 1500 ml double-walled reactor and concentrated under vacuum and 360 g of o-xylene are recovered. The reddish-yellow residue is cooled to 70° C. and 636 g of methanol are added cautiously from a dropping funnel, while keeping the temperature at 60°–65° C. The solution is seeded and stirred for c. 30 minutes at 60°–65° C. to effect crystallisation. The crystalline slurry is then cooled over 2 hours to −5° C. and stirring is continued at this temperature for a further 1 hour. The crystals are collected by suction filtration and the residue is washed with 400 g of cold (−5° C.) methanol in 5 portions. The well dry-pressed product is dried in a vacuum drier at 50°–60° C., yielding 266 g of a white solid. Analysis by gas chromatography shows this material to consist of c. 85% of 3-(3,4-dimethylphenyl)-5,7-di-tert-butyl-3H-benzofuran-2-one (compound (103), Table 1) as well as of c. 15% of the 3-(2,3-dimethylphenyl)-5,7-di-tert-butyl-3H-benzofuran-2-one isomer (compound (103A)).

EXAMPLE 13

Preparation of 3-(N-methylcarbamoyloxy)-5-methyl-7-tert-butyl-3H-benzofuran-2-one (compound (212), Table 2).

A mixture of 5.5 g (25.0 mmol) of 7-tert-butyl-3-hydroxy-5-methyl-3H-benzofuran-2-one (compound (202), Example 1a), 3 ml (50.0 mmol) of methyl isocyanate and 2 drops of methanesulfonic acid are refluxed for 3 1/4 hours. Then a further 3 ml (50.0 mmol) of methyl isocyanate and 2 drops of methanesulfonic acid are added. The reaction mixture is refluxed for another 16 hours, then cooled, diluted with dichloromethane and washed with water and a 5% aqueous solution of sodium hydrogencarbonate. The organic phases are combined, dried over magnesium sulfate and concentrated on a vacuum rotary evaporator. Crystallisation of the residue from toluene yields 4.45 g (65%) of 3-(N-methylcarbamoyloxy)-5-methyl-7-tert-butyl-3H-benzofuran-2-one, m.p. 138°–143° C. (compound (212), Table 2).

EXAMPLE 14

Preparation of 7-tert-butyl-3-chloro-5-methyl-3H-benzofuran-2-one (compound (208), Table 2).

To a suspension of 2.2 g (10.0 mmol) of 7-tert-butyl-3-hydroxy-5-methyl-3H-benzofuran-2-one (compound (202), Example 1a, Table 2) in 2.4 ml (55.0 mol) of thionyl chloride is added one drop of dimethyl formamide and the mixture is stirred for 2 hours at room temperature. Excess thionyl chloride is afterwards distilled off on a vacuum rotary evaporator. Chromatography of the residue on silica gel with the solvent system dichloromethane/hexane=1:1 and crystallisation of the pure fractions from methanol yields 0.30 g (13%) of 7-tert-butyl-3-chloro-5-methyl-3H-benzofuran-2-one, m.p. 81°–86° C. (compound (208), Table 2).

TABLE 1

| No. | Compound | m.p. (°C.) | C (%), H (%) (calcd/found) | | Yield (%) |
|---|---|---|---|---|---|
| 101 | | 93–97 | 82.24 82.10 | 8.63 8.66 | 80 |
| 102 | | 92–96 | 82.24 82.19 | 86.3 8.78 | 52[a] |
| 103 | | 130–132 | 82.24 82.36 | 8.63 8.62 | 69[a] |
| 104 | | 130–133 | 82.10 82.13 | 8.39 8.31 | 42[a] |
| 105 | | 127–132 | 82.24 82.39 | 8.63 8.65 | 47[a] |

TABLE 1-continued

| | Structure | mp (°C) | NMR / characterization | Yield (%) |
|---|---|---|---|---|
| 106 | 3,5-di-tert-butyl-2-methylphenyl / 4-isopropylphenyl acetic acid derivative | 109–115 | 82.37  8.85<br>82.24  8.91 | 41[a] |
| 107 | 3,5-di-tert-butyl-2-methylphenyl / 4-tert-butylphenyl acetic acid derivative | 110–115 | 82.49  9.05<br>82.49  9.03 | 68[a] |
| 108 | 3,5-di-tert-butyl-2-methylphenyl / phenyl acetic acid derivative | 116–119 | characterised by $^1$H-NMR (CDCl$_3$) δ(H*) = 4.84 ppm | 64 |
| 109 | 3,5-di-tert-butyl-2-methylphenyl / 4-dodecylphenyl acetic acid derivative | Oel | characterised by $^1$H-NMR (CDCl$_3$) δ(H*) = 4.84 ppm | 66[a] |
| 110 | 3,5-di-tert-butyl-2-methylphenyl / 2,3,4-trimethylphenyl acetic acid derivative | 118–122 | 82.37  8.85<br>82.31  8.84 | 74[a] |
| 111 | 3,5-di-tert-butyl-2-methylphenyl / 2,3,4,5,6-pentamethylphenyl acetic acid derivative | 185–190 | 82.61  9.24<br>82.41  9.43 | 89 |

TABLE 1-continued

| No. | Structure | mp (°C) | NMR | Yield |
|---|---|---|---|---|
| 112 | (3,5-di-tert-butyl... structure) | 69–80 | 81.60 / 7.53; 81.42 / 7.57 | 70[a] |
| 113 | (3-(1-methylpentadecyl)... structure) | oil | characterised by $^1$H-NMR (CDCl$_3$) δ(H*) = 4.85 ppm | 56 |
| 114 | (3,5-dicyclohexyl... structure) | resin | characterised by $^1$H-NMR (CDCl$_3$) δ(H*) = 4.86 ppm | 57 |
| 115 | (3,5-di-tert-butyl, 3',5'-dimethyl-4'-hydroxyphenyl structure) | 225–228 | characterised by $^1$H-NMR (CDCl$_3$) δ(H*) = 4.70 ppm | 78[a] |
| 116 | (3,5-di-tert-butyl, 3',5'-dimethyl-4'-methoxyphenyl structure) | 133–135 | characterised by $^1$H-NMR (CDCl$_3$) δ(H*) = 4.72 ppm | 52[a] |
| 117 | (3,5-di-tert-butyl, 4'-methoxyphenyl structure) | 102–104 | characterised by $^1$H-NMR (CDCl$_3$) δ(H*) = 4.78 ppm | 65[a] |

TABLE 1-continued

| No. | Compound | m.p. (°C.) | (calcd/found) | Yield (%) |
|-----|----------|-----------|---------------|-----------|
| 118 | [structure: 3,5-di-tert-butyl-2-methylphenyl group attached to CH* bearing carboxylate and 4-(2-acetoxyethoxy)phenyl] | 91–94 | characterised by $^1$H-NMR (CDCl$_3$) δ(H*) = 4.78 ppm | 23[a] |
| 119 | [structure: 3,5-di-tert-butyl-2-methylphenyl group attached to CH* bearing carboxylate and 4-(methylthio)phenyl (SCH$_3$)] | 125–131 | characterised by $^1$H-NMR (CDCl$_3$) δ(H*) = 4.79 ppm | 18[a] |
| 120 | [structure: 3,5-di-tert-butyl-2-methylphenyl group attached to CH bearing carboxylate and 4-chlorophenyl] | 121–126 | 74.04    7.06<br>74.02    7.11 | 37[a] |

[a] The product may additionally contain minor amounts of other structural isomers in accordance with the substitution at the phenyl ring in 3-position of the benzofuran-2-one.

| No. | Compound | m.p. (°C.) | (calcd/found) | Yield (%) |
|-----|----------|-----------|---------------|-----------|
|     |          |           | C (%), H (%), N (%) |     |
| 121 | [bis-structure: two 3,5-di-tert-butyl-2-methylphenyl benzofuranone units linked through 4,4'-(N-methylamino)diphenyl bridge] | 135–145 | 80.44   7.95   2.08<br>80.20   8.06   1.96 | 56[a] |
| 122 | [structure: 3,5-di-tert-butyl-2-methylphenyl group attached to CH bearing carboxylate and 4-biphenyl] | 168–170 | 84.38   7.57<br>84.23   7.66 | 25[a] |

C (%), H (%), S (%)

TABLE 1-continued

| No. | Compound | m.p. (°C.) | C (%), H (%) (calcd/found) | | Yield (%) |
|---|---|---|---|---|---|
| 123 | [structure: 3,5-di-tert-butyl-benzofuranone with thiophene substituent] | 86–93 | 73.13 73.10 | 7.37 9.76 7.38 9.69 | 11[a] |
| 124 | [structure: bis-benzofuranone linked via cyclohexyl with two dimethylphenyl groups] | 220–228 | 82.60 82.58 | 7.84 7.85 | 40 |

[a] The product may additionally contain minor amounts of other structural isomers in accordance with the substitution at the phenyl ring in 3-position of the benzofuran-2-one.

| No. | Compound | m.p. (°C.) | C (%), H (%) (calcd/found) | Yield (%) |
|---|---|---|---|---|
| 125 | [structure: 3,5-di-tert-butyl benzofuranone with dibenzofuranyl substituent] | 142–154 | 81.52 6.84 80.97 6.5 | 33[a] |
| 126 | [structure: 3,5-di-tert-butyl benzofuranone with phenanthrenyl substituent] | 186–189 | 85.27 7.16 85.15 7.20 | 17[a] |
| 127 | [structure: bis-benzofuranone linked via diphenyl ether] | Harz | characterised by $^1$H-NMR (CDCl$_3$) δ(H*) = 4.82 ppm | 31[a] |
| 128 | [structure: 3,5-di-tert-butyl benzofuranone with N-methylcarbazolyl substituent] | 84–90 | 81.43 6,57 81.37 6,72 | 10[a] |

TABLE 1-continued

[a] The product may additionally contain minor amounts of other structural isomers in accordance with the substitution at the aryl ring in 3-position of the benzofuran-2-one.

| No. | Compound | m.p. | C (%), H (%) (calcd/found) | | Yield |
|---|---|---|---|---|---|
| 129 | 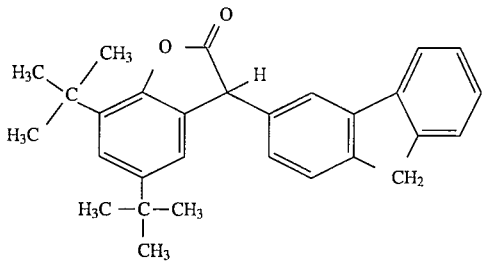 | 140–153 | 84.84 84.66 | 7.37 7.52 | 17[a] |

[a] The product may additionally contain minor amounts of other structural isomers in accordance with the substitution at the fluorene ring in 3-position of the benzofuran-2-one.

TABLE 2

| No. | Compound | m.p. (°C.) | C (%), H (%) (calcd/found) | | Yield (%) |
|---|---|---|---|---|---|
| 201 | | resin | 73.25 73.33 | 8.45 8.50 | 100 |
| 202 | | 152–160 | 70.89 70.40 | 7.32 7.40 | 82 |
| 203 | | resin | characterised by $^1$H-NMR (CDCl$_3$) δ(H*) = 5.33 ppm | | 45[a] |
| 204 | | resin | characterised by $^1$H-NMR (CDCl$_3$) δ(H*) = 5.30 ppm | | ~100 |

TABLE 2-continued

| No. | Compound | m.p. (°C.) | C (%), H (%) (calcd/found) | Yield (%) |
|---|---|---|---|---|
| 205 | (structure: 3-isopentadecyl-5-methyl-2-methyl-phenyl with CH(OH)C(=O)O- group, H*) | resin | characterised by $^1$H-NMR (CDCl$_3$) δ(H*) = 5.31 ppm | 98 |
| 206 | (structure: 3-tert-butyl-5-tert-butyl-2-methyl-phenyl with CH(OC(=O)CH$_3$)C(=O)O- group) | resin | 71.03   7.95<br>71.10   7.98 | 92 |
| 207 | (bis-structure linked via cyclohexyl-CH, two 3-tert-butyl-2-methyl-phenyl groups each with CH(OH)C(=O)O-) | resin | characterised by $^1$H-NMR (CDCl$_3$) δ(tert-butyl) = 1.34 ppm | ~100 |
| 208 | (structure: 3-tert-butyl-5-methyl-2-methyl-phenyl with CH(Cl)C(=O)O- group, H*) | 81–86 | characterised by $^1$H-NMR (CDCl$_3$) δ(H*) = 5.34 ppm | 13 |
| 209 | (structure: 3-tert-butyl-5-(CH$_2$)$_2$COOH-2-methyl-phenyl with CH(Cl)C(=O)O- group, H*) | resin | characterised by $^1$H-NMR (CDCl$_3$) δ(H*) = 5.29 ppm | ~100 |
| 210 | (structure: 3-(1-methyl-1-phenylethyl)-5-(1-methyl-1-phenylethyl)-2-methyl-phenyl with CH(OH)C(=O)O- group, H*) | resin | characterised by $^1$H-NMR (CDCl$_3$) δ(H*) = 5.08 ppm | 38 |

TABLE 2-continued

| No. | Compound | m.p. (°C.) | C (%), H (%) (calcd/found) | Yield (%) |
|---|---|---|---|---|
| 211 | 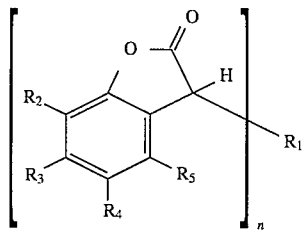 | 100–103 | 73.88  8.75<br>73.73  8.75 | 61 |
| 212 | 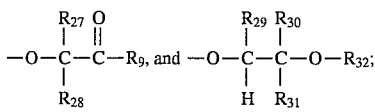 | 138–143 | 64.97  6.91<br>65.02  6.89 | 65 | a)chromatographed on silica gel ($CH_2Cl_2$/hexane = 4:1)

What is claimed is:

1. A process for the preparation of a compound of formula I $$\left[ \begin{array}{c} \text{structure with } R_1, R_2, R_3, R_4, R_5 \end{array} \right]_n \quad (I)$$

wherein, when n is 1, $R_1$ is phenyl, naphthyl, phenanthryl, anthryl, 5,6,7,8-tetrahydro-2-naphthyl, thienyl, benzo[b]thienyl, naphtho[2,3-b]thienyl, thiathrenyl, furyl, benzofuryl, isobenzofuryl, dibenzofuryl, chromenyl, xanthenyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, tetralinyl, fluorenyl or phenoxazinyl, which is optionally substituted by one or more substituents selected, independently of the other, from the group consisting of halogen, hydroxy, $C_1$–$C_{25}$alkyl, $C_2$–$C_{25}$alkyl which is interrupted by oxygen, sulfur or >N—$R_8$; $C_1$–$C_{25}$alkoxy, $C_2$–$C_{25}$alkoxy which is interrupted by oxygen, sulfur or >N—$R_8$; $C_1$–$C_{25}$alkylthio, $C_3$–$C_{25}$alkenyl, $C_3$–$C_{25}$alkenyloxy, $C_3$–$C_{25}$alkynyl, $C_3$–$C_{25}$alkynyloxy, $C_7$–$C_9$-phenylalkyl, $C_7$–$C_9$phenylalkoxy, unsubstituted or $C_1$–$C_4$alkyl-substituted phenyl; unsubstituted or $C_1$–$C_4$alkyl-substituted phenoxy; unsubstituted or $C_1$–$C_4$alkyl-substituted $C_5$–$C_8$cycloalkyl; unsubstituted or $C_1$–$C_4$alkyl-substituted $C_5$–$C_8$cycloalkoxy; $C_1$–$C_4$alkylamino, di($C_1$–$C_4$alkyl)amino, $C_1$–$C_{25}$alkanoyl, $C_3$–$C_{25}$alkanoyl which is interrupted by oxygen, sulfur or >N—$R_8$; $C_1$–$C_{25}$alkanoyloxy, $C_3$–$C_{25}$alkanoyloxy which is interrupted by oxygen, sulfur or >N—$R_8$; $C_1$–$C_{25}$alkanoylamino, $C_3$–$C_{25}$alkenoyl, $C_3$–$C_{25}$alkenoyl which is interrupted by oxygen, sulfur or >N—$R_8$; $C_3$–$C_{25}$alkenoyloxy, $C_3$–$C_{25}$alkanoyloxy which is interrupted by oxygen, sulfur or >N—$R_8$; $C_6$–$C_9$cycloalkylcarbonyl, $C_6$–$C_9$cycloalkylcarbonyloxy, benzoyl or $C_1$–$C_{12}$alkyl-substituted benzoyl; benzoyloxy or $C_1$–$C_{12}$alkyl-substituted benzoyloxy;

$$-O-\underset{R_{28}}{\underset{|}{C}}-\underset{}{\overset{O}{\overset{\|}{C}}}-R_9, \text{ and } -O-\underset{H}{\underset{|}{C}}-\underset{R_{31}}{\underset{|}{\overset{R_{29}}{\overset{|}{C}}}}\underset{}{\overset{R_{30}}{\overset{|}{-O-R_{32}}}};$$

or where a pair of substituents, together with the linking carbon atoms, forms a benzene ring, where $R_8$ and $R_9$ are as defined below, $R_{27}$ and $R_{28}$ are each independently of the other hydrogen, $C_1$–$C_4$alkyl or phenyl, $R_{29}$ is hydrogen or $C_1$–$C_4$alkyl, $R_{30}$ is hydrogen, unsubstituted or $C_1$–$C_4$alkyl-substituted phenyl; $C_1$–$C_{25}$alkyl, $C_2$–$C_{25}$alkyl which is interrupted by oxygen, sulfur or >N—$R_8$; $C_7$–$C_9$phenylalkyl which is unsubstituted or substituted at the phenyl moiety by 1 to 3 $C_1$–$C_4$alkyl groups; $C_7$–$C_{25}$phenylalkyl which is interrupted by oxygen, sulfur or >N—$R_8$ or is unsubstituted or substituted in the phenyl moiety by 1 to 3 $C_1$–$C_4$alkyl groups; or $R_{29}$ and $R_{30}$, together with the linking carbon atoms, form a $C_5$–$C_{12}$cycloalkylene ring which is unsubstituted or substituted by 1 to 3 $C_1$–$C_4$alkyl groups, $R_{31}$ is hydrogen or $C_1$–$C_4$alkyl, $R_{32}$ is hydrogen, $C_1$–$C_{25}$alkanoyl, $C_3$–$C_{25}$alkenoyl, $C_3$–$C_{25}$alkanoyl which is interrupted by oxygen, sulfur or >N—$R_8$; $C_2$–$C_{25}$alkanoyl which is substituted by a di($C_1$–$C_6$alkyl)phosphonate group; $C_6$–$C_9$cycloalkylcarbonyl, thenoyl, furoyl, benzoyl or $C_1$–$C_{12}$alkyl-substituted benzoyl;

[Structure: -C(=O)-C_sH_{2s}- attached to phenyl ring with C(CH_3)_3 at top, OH, and R_{33}]

[Structure: -C(=O)-CH_2-S-CH_2- attached to phenyl ring with C(CH_3)_3, OH, and R_{33}]

[Structure: [-C(=O)-CH_2-C(CH_3)- attached to phenyl ring with C(CH_3)_3, OH, and R_{33}]_2]

$$-\overset{O}{\underset{\|}{C}}-R_{34}-\overset{O}{\underset{\|}{C}}-R_{35} \text{ or } -\overset{O}{\underset{\|}{C}}-R_{36}-R_{37},$$

$R_{33}$ is hydrogen or $C_1$–$C_8$alkyl, $R_{34}$ is a direct bond, $C_1$–$C_{18}$alkylene, $C_2$–$C_{18}$alkylene which is interrupted by oxygen, sulfur or >N—$R_8$; $C_2$–$C_{18}$alkenylene, $C_2$–$C_{20}$alkylidene, $C_7$–$C_{20}$phenylalkylidene, $C_5$–$C_8$cycloalkylene, $C_7$–$C_8$bicycloalkylene, unsubstituted or $C_1$–$C_4$alkyl-substituted phenylene,

[furan-2,5-diyl] or [thiophene-2,5-diyl], $R_{35}$ is hydroxy, $\left[ -O^{\ominus}\frac{1}{r}M^{r+} \right]$, $C_1$–$C_{18}$alkoxy or $-N\begin{matrix}R_{12}\\ \\R_{13}\end{matrix}$, $R_{36}$ is oxygen, —NH— or $>N-\overset{O}{\underset{\|}{C}}-NH-R_{37}$, $R_{37}$ is $C_1$–$C_{18}$alkyl or phenyl, and
s is 0, 1 or 2,
when n is 2,
$R_1$ is unsubstituted or $C_1$–$C_4$alkyl- or hydroxy-substituted phenylene or naphthylene; or is —$R_6$—X—$R_7$—, $R_2$, $R_3$, $R_4$ and $R_5$ are each independently of one another hydrogen, chloro, hydroxy, $C_1$–$C_{25}$alkyl, $C_7$–$C_9$-phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di-($C_1$–$C_4$alkyl)amino, $C_1$–$C_{25}$alkanoyloxy, $C_1$–$C_{25}$alkanoylamino, $C_3$–$C_{25}$alkenoyloxy, $C_3$–$C_{25}$alkanoyloxy which is interrupted by oxygen, sulfur or >N—$R_8$; $C_6$–$C_9$cycloalkylcarbonyloxy, benzoyloxy or $C_1$–$C_{12}$alkyl-substituted benzoyloxy; or each pair of substituents $R_2$ and $R_3$ or $R_3$ and $R_4$ or $R_4$ and $R_5$, together with the linking carbon atoms, forms a benzene ring; $R_4$ is additionally —$(CH_2)_p$—$COR_9$ or —$(CH_2)_q$OH, or, if $R_3$ and $R_5$ are hydrogen, $R_4$ is additionally a radical of formula II $$\text{(II)}$$

[Structure: benzene ring with R_2 (ortho), CH(R_1)-O-C(=O)- group, and R_{10}-C(-R_{11})- substituent]

wherein $R_1$ is as defined above when n=1, $R_6$ and $R_7$ are each independently of the other unsubstituted or $C_1$–$C_4$alkyl-substituted phenylene or naphthylene, $R_8$ is hydrogen or $C_1$–$C_8$alkyl, $R_9$ is hydroxy, $\left[ -O^{\ominus}\frac{1}{r}M^{r+} \right]$, $C_1$–$C_{18}$alkoxy or $-N\begin{matrix}R_{12}\\ \\R_{13}\end{matrix}$, $R_{10}$ and $R_{11}$ are each independently of the other hydrogen, $CF_3$, $C_1$–$C_{12}$alkyl or phenyl, or $R_{10}$ and $R_{11}$, together with the linking carbon atom, form a $C_5$–$C_8$cycloalkylidene ring which is unsubstituted or substituted by 1 to 3 $C_1$–$C_4$alkyl groups, $R_{12}$ and $R_{13}$ are each independently of the other hydrogen or $C_1$–$C_{18}$alkyl, $R_{14}$ is hydrogen or $C_1$–$C_{18}$alkyl, M is a metal cation of valency r, X is a direct bond, oxygen, sulfur or —$NR_{14}$—, n is 1 or 2, p is 0, 1 or 2, q is 1, 2, 3, 4, 5 or 6, and r is 1, 2 or 3, which process comprises reacting a compound of formula III

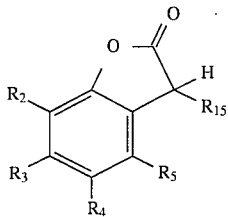
(III)

wherein $R_{15}$ is halogen or $-OR'_{15}$, $R'_{15}$ is hydrogen, $C_1-C_{25}$alkanoyl, $C_3-C_{25}$alkenoyl, $C_3-C_{25}$alkanoyl which is interrupted by oxygen, sulfur or $>N-R_8$; $C_6-C_9$cycloalkylcarbonyl, thenoyl, furoyl, benzoyl or $C_1-C_{12}$alkyl-substituted benzoyl; naphthoyl or $C_1-C_{12}$alkyl-substituted naphthoyl; $C_1-C_{25}$alkanesulfonyl, fluoro-substituted $C_1-C_{25}$alkanesulfonyl; phenylsulfonyl or $C_1-C_{12}$alkyl-substituted phenylsulfonyl;

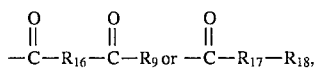

$R_{16}$ is a directe bond, $C_1-C_{18}$alkylene, $C_2-C_{18}$alkylene which is interrupted by oxygen, sulfur or $>N-R_8$; $C_2-C_{18}$alkenylene, $C_2-C_{20}$alkylidene, $C_7-C_{20}$phenylalkylidene, $C_5-C_8$cycloalkylene, $C_7-C_8$bicycloalkylene, unsubstituted or $C_1-C_4$alkyl-substituted phenylene,

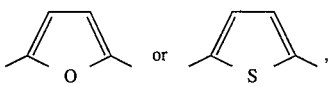

$R_{17}$ is oxygen, $-NH-$ or

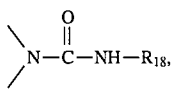

and $R_{18}$ is $C_1-C_{18}$alkyl or phenyl, with a compound of formula IV $[H]_n-R_1$ (IV).

2. A process for the preparation of a compound of formula I

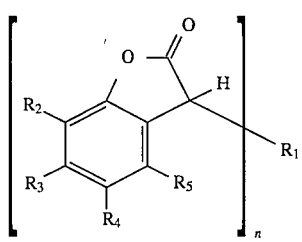
(I)

wherein $R_1$, $R_2$, $R_3$, $R_4$, $R_5$ and n are as defined in claim 1, which comprises reacting one equivalent of the phenol of formula VII

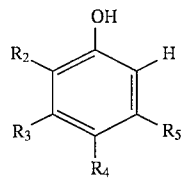
(VII)

wherein $R_2$, $R_3$, $R_4$ and $R_5$ are as defined in claim 1, with 0.8 to 2.0 equivalents of glyoxylic acid to form a compound of formula VIII

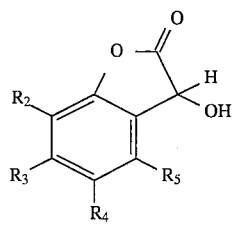
(VIII)

wherein $R_2$, $R_3$, $R_4$ and $R_5$ are as defined in claim 1, and subsequently reacting said compound of formula VIII, without isolation, with a compound of formula IV $[H]_n-R_1$ (IV)

wherein $R_1$ and n as defined in claim 1.

3. A process according to claim 2, which comprises reacting the compound of formula VIII, without isolation before the further reaction with a compound of formula IV, in an additional reaction step with a hydrohalic acid, a halide of an oxysulfuric acid, a halide of phosphoric acid, a halide of a phosphorous acid, an acid of formula IX $R'_{15}-OH$ (IX)

an acid halide of formula X, $R'_{15}-Y$ (X)

an ester of formula XI $R'_{15}-O-R_{38}$ (XI)

a symmetrical or unsymmetrical anhydride of formula XII $R'-O-R'_{15}$ (XII)

or an isocyanate of formula XIII $R_{39}-N=C=O$ (XIII)

wherein $R'_{15}$ in formulae IX, X, XI and XII is as defined in claim 1, with the proviso that $R'_{15}$ is not hydrogen;

$R_{38}$ is $C_1-C_8$alkyl, $R_{39}$ is $C_1-C_{18}$alkyl or phenyl, and

Y is fluoro, chloro, bromo or iodo, to form a compound of formula III

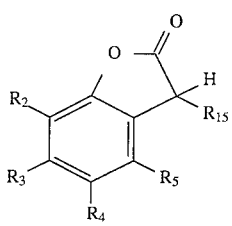

(III)

wherein the substituents $R_2$, $R_3$, $R_4$, $R_5$ and $R_{15}$ are as defined in claim 1, with the proviso that, when $R_{15}=-OR'_{15}$, $R'_{15}$ is not hydrogen.

4. A process according to claim 1, wherein, when n is 1, $R_1$ is phenanthryl, thienyl, dibenzofuryl, unsubstituted or $C_1-C_4$alkyl-substituted carbazolyl; or is fluorenyl, or $R_1$ is a radical of formula V or VI

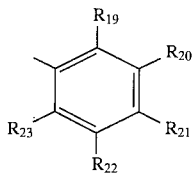

(V)

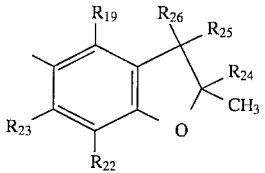

(VI)

wherein $R_{19}$, $R_{20}$, $R_{21}$, $R_{22}$ and $R_{23}$ are each independently of one another hydrogen, halogen, hydroxy, $C_1-C_{25}$alkyl, $C_2-C_{25}$alkyl which is interrupted by oxygen, sulfur or $>N-R_8$; $C_1-C_{25}$alkoxy, $C_2-C_{25}$alkoxy which is interrupted by oxygen, sulfur or $>N-R_8$; $C_1-C_{25}$alkylthio, $C_3-C_{25}$alkenyl, $C_3-C_{25}$alkenyloxy, $C_3-C_{25}$alkynyl, $C_3-C_{25}$alkynyloxy, $C_7-C_9$phenylalkyl, $C_7-C_9$phenylalkoxy, unsubstituted or $C_1-C_4$alkyl-substituted phenyl; unsubstituted or $C_1-C_4$alkyl-substituted phenoxy; unsubstituted or $C_1-C_4$alkyl-substituted $C_5-C_8$-cycloalkyl; unsubstituted or $C_1-C_4$alkyl-substituted $C_5-C_8$cycloalkoxy; $C_1-C_4$alkylamino, di($C_1-C_4$alkyl)amino, $C_1-C_{25}$alkanoyl, $C_3-C_{25}$alkanoyl which is interrupted by oxygen, sulfur or $>N-R_8$; $C_1-C_{25}$-alkanoyloxy, $C_3-C_{25}$alkanoyloxy which is interrupted by oxygen, sulfur or $>N-R_8$; $C_1-C_{25}$alkanoylamino, $C_3-C_{25}$alkenoyl, $C_3-C_{25}$alkenoyl which is interrupted by oxygen, sulfur or $>N-R_8$; $C_3-C_{25}$alkenoyloxy, $C_3-C_{25}$alkenoyloxy which is interrupted by oxygen, sulfur or $>N-R_8$; $C_6-C_9$cycloalkylcarbonyl, $C_6-C_9$cycloalkylcarbonyloxy, benzoyl or $C_1-C_{12}$alkyl-substituted benzoyl; benzoyloxy or $C_1-C_{12}$alkyl-substituted benzoyloxy;

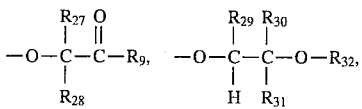

or in formula V each pair of substituents $R_{19}$ and $R_{20}$ or $R_{20}$ and $R_{21}$, together with the linking carbon atoms, forms a benzene ring, $R_{24}$ is hydrogen, $C_1-C_4$alkyl, unsubstituted or $C_1-C_4$alkyl-substituted phenyl, $R_{25}$ and $R_{26}$ are hydrogen, $C_1-C_4$alkyl or phenyl, with the proviso that at least one of $R_{25}$ and $R_{26}$ is hydrogen, $R_{27}$ and $R_{28}$ are each independently of the other hydrogen, $C_1-C_4$alkyl or phenyl, $R_{29}$ is hydrogen or $C_1-C_4$alkyl, $R_{30}$ is hydrogen, unsubstituted or $C_1-C_4$alkyl-substituted phenyl; $C_1-C_{25}$alkyl, $C_2-C_{25}$alkyl which is interrupted by oxygen, sulfur or $>N-R_8$; $C_7-C_9$phenylalkyl which is unsubstituted or substituted at the phenyl moiety by 1 to 3 $C_1-C_4$alkyl groups; $C_7-C_{25}$phenylalkyl which is interrupted by oxygen, sulfur or $>N-R_8$ or is unsubstituted or substituted in the phenyl moiety by 1 to 3 $C_1-C_4$alkyl groups; or $R_{29}$ and $R_{30}$, together with the linking carbon atoms, form a $C_5-C_{12}$cycloalkylene ring which is unsubstituted or substituted by 1 to 3 $C_1-C_4$alkyl groups, $R_{31}$ is hydrogen or $C_1-C_4$alkyl, $R_{32}$ is hydrogen, $C_1-C_{25}$alkanoyl, $C_3-C_{25}$alkenoyl, $C_3-C_{25}$alkanoyl which is interrupted by oxygen, sulfur or $>N-R_8$; $C_2-C_{25}$alkanoyl which is substituted by a di($C_1-C_6$alkyl)-phosphonate group; $C_6-C_9$cycloalkylcarbonyl, thenoyl, furoyl, benzoyl or $C_1-C_{12}$alkyl-substituted benzoyl;

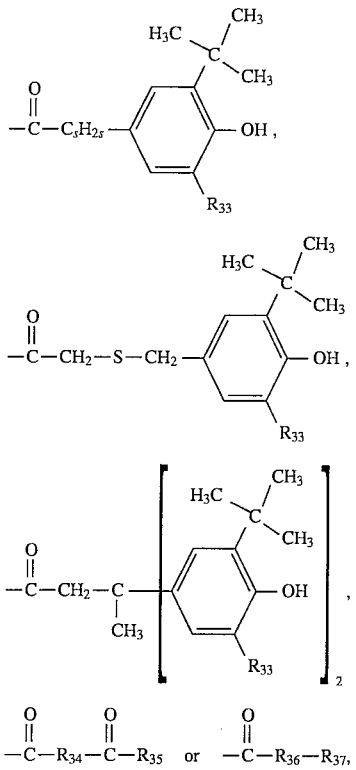

$R_{33}$ is hydrogen or $C_1-C_8$alkyl, $R_{34}$ is a direct bond, $C_1-C_{18}$alkylene, $C_2-C_{18}$alkylene which is interrupted by oxygen, sulfur or $>N-R_8$; $C_2-C_{18}$alkenylene, $C_2-C_{20}$alkylidene, $C_7-C_{20}$phenylalkylidene, $C_5-C_8$cycloalkylene, $C_7-C_8$bicycloalkylene, unsubstituted or $C_1-C_4$alkyl-substituted phenylene,

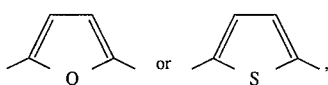

$R_{35}$ is hydroxy,

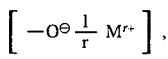

$C_1$–$C_{18}$alkoxy or

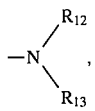

$R_{36}$ is oxygen, —NH— or

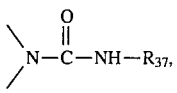

$R_{37}$ is $C_1$–$C_{18}$alkyl or phenyl, and s is 0, 1 or 2.

5. A process according to claim 1, wherein, when n is 2, $R_1$ is —$R_6$—X—$R_7$—, $R_6$ and $R_7$ are phenylene, X is oxygen or —$NR_{14}$—, and $R_{14}$ is $C_1$–$C_4$alkyl.

6. A process according to claim 4, wherein $R_{19}$, $R_{20}$, $R_{21}$, $R_{22}$ and $R_{23}$ are each independently of one another hydrogen, chloro, bromo, hydroxy, $C_1$–$C_{18}$alkyl, $C_2$–$C_{18}$alkyl which is interrupted by oxygen or sulfur;

$C_1$–$C_{18}$alkoxy, $C_2$–$C_{18}$alkoxy which is interrupted by oxygen or sulfur; $C_1$–$C_{18}$alkylthio, $C_3$–$C_{12}$alkenyloxy, $C_3$–$C_{12}$alkynyloxy, $C_7$–$C_9$phenylalkyl, $C_7$–$C_9$phenylalkoxy, unsubstituted or $C_1$–$C_4$alkyl-substituted phenyl; phenoxy, cyclohexyl, $C_5$–$C_8$cycloalkoxy; $C_1$–$C_4$alkylamino, di($C_1$–$C_4$alkyl)amino, $C_1$–$C_{12}$alkanoyl, $C_3$–$C_{12}$alkanoyl which is interrupted by oxygen or sulfur; $C_1$–$C_{12}$alkanoyloxy, $C_3$–$C_{12}$alkanoyloxy which is interrupted by oxygen or sulfur; $C_1$–$C_{12}$alkanoylamino, $C_3$–$C_{12}$alkenoyl, $C_3$–$C_{12}$alkenoyloxy, cyclohexylcarbonyl, cyclohexylcarbonyloxy, benzoyl or $C_1$–$C_4$alkyl-substituted benzoyl; benzoyloxy or $C_1$–$C_4$alkyl substituted benzoyloxy;

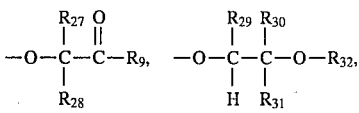

or in formula V each pair of substituents $R_{19}$ and $R_{20}$ or $R_{20}$ and $R_{21}$, together with the linking carbon atoms, forms a benzene ring, $R_{24}$ is hydrogen or $C_1$–$C_4$alkyl, $R_{25}$ and $R_{26}$ are hydrogen or $C_1$–$C_4$alkyl, with the proviso that at least one of $R_{25}$ and $R_{26}$ is hydrogen, $R_{27}$ and $R_{28}$ are each independently of the other hydrogen or $C_1$–$C_4$alkyl, $R_{29}$ is hydrogen, $R_{30}$ is hydrogen, phenyl, $C_1$–$C_{18}$alkyl, $C_2$–$C_{18}$alkyl which is interrupted by oxygen or sulfur; $C_7$–$C_9$phenylalkyl, $C_7$–$C_{18}$phenylalkyl which is interrupted by oxygen or sulfur and unsubstituted or substituted in the phenyl moiety by 1 to 3 $C_1$–$C_4$alkyl groups, and $R_{29}$ and $R_{30}$, together with the linking carbon atoms, form a cyclohexylene ring which is unsubstituted or substituted by 1 to 3 $C_1$–$C_4$alkyl groups, $R_{31}$ is hydrogen or $C_1$–$C_4$alkyl, $R_{32}$ is hydrogen, $C_1$–$C_{18}$alkanoyl, $C_3$–$C_{12}$alkenoyl, $C_3$–$C_{12}$alkanoyl which is interrupted by oxygen or sulfur; $C_2$–$C_{12}$alkanoyl which is substituted by a di($C_1$–$C_6$-alkyl)phosphonate group; $C_6$–$C_9$cycloalkylcarbonyl, benzoyl,

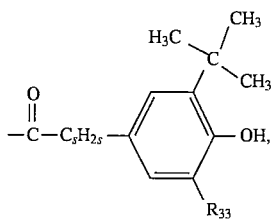

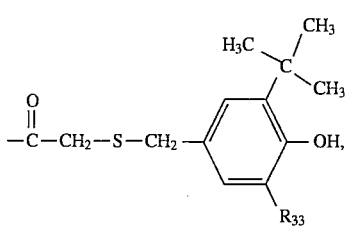

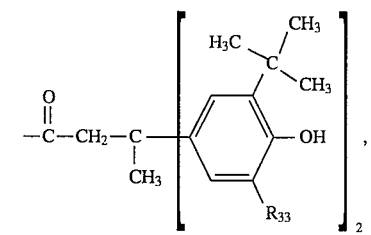

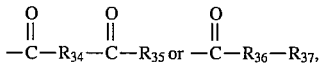

$R_{33}$ is hydrogen or $C_1$–$C_4$alkyl, $R_{34}$ is $C_1$–$C_{12}$alkylene, $C_2$–$C_8$alkenylene, $C_2$–$C_8$alkylidene, $C_7$–$C_{12}$phenylalkylidene, $C_5$–$C_8$cycloalkylene or phenylene, $R_{35}$ is hydroxy,

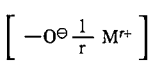

or $C_1$–$C_{18}$alkoxy, $R_{36}$ is oxygen or —NH—, $R_{37}$ is $C_1$–$C_8$alkyl or phenyl, and s is 1 or 2.

7. A process according to claim 4, wherein $R_1$ is phenanthryl, thienyl, dibenzofuryl, unsubstituted or $C_1$–$C_4$alkyl-substituted carbazolyl; or fluorenyl, or $R_1$ is a radical of formula V

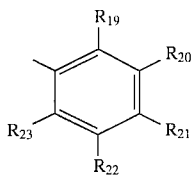
(V)

wherein $R_{19}$, $R_{20}$, $R_{21}$, $R_{22}$ and $R_{23}$ are each independently of one another hydrogen, chloro, hydroxy, $C_1$–$C_{18}$alkyl, $C_1$–$C_{18}$alkoxy, $C_1$–$C_{18}$alkylthio, $C_3$–$C_4$alkenyloxy, $C_3$–$C_4$-alkynyloxy phenyl, benzoyl, benzoyloxy or

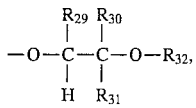

$R_{29}$ is hydrogen, $R_{30}$ is hydrogen, phenyl or $C_1$–$C_{18}$alkyl, or $R_{29}$ and $R_{30}$, together with the linking carbon atoms, form a cyclohexylene ring which is unsubstituted or substituted by 1 to 3 $C_1$–$C_4$alkyl groups, $R_{31}$ is hydrogen or $C_1$–$C_4$alkyl, and $R_{32}$ is hydrogen, $C_1$–$C_{12}$alkanoyl or benzoyl.

8. A process according to claim 7, wherein $R_{19}$ is hydrogen or $C_1$–$C_4$alkyl, $R_{20}$ is hydrogen or $C_1$–$C_4$alkyl, $R_{21}$ is hydrogen, chloro, hydroxy, $C_1$–$C_{12}$alkyl, $C_1$–$C_4$alkoxy, $C_1$–$C_4$alkylthio, phenyl or —O—$CH_2$—$CH_2$—O—$R_{32}$, $R_{22}$ is hydrogen or $C_1$–$C_4$alkyl, $R_{23}$ is hydrogen or $C_1$–$C_4$alkyl, and $R_{32}$ is $C_1$–$C_4$alkanoyl.

9. A process according to claim 1, wherein $R_2$, $R_3$, $R_4$ and $R_5$ are each independently of one another hydrogen, chloro, hydroxy, $C_1$–$C_{25}$alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{12}$alkoxy, $C_1$–$C_{12}$alkylthio, $C_1$–$C_4$alkylamino, di($C_1$–$C_4$alkyl)amino, $C_1$–$C_{18}$alkanoyloxy, $C_1$–$C_{18}$alkanoylamino, $C_3$–$C_{18}$alkenyloxy, $C_3$–$C_{18}$alkanoyloxy which is interrupted by oxygen, sulfur or >N—$R_8$; $C_6$–$C_9$-cycloalkylcarbonyloxy, benzoyloxy or $C_1$–$C_8$alkyl-substituted benzoyloxy, or each pair of substituents $R_2$ and $R_3$ or $R_3$ and $R_4$ or $R_4$ and $R_5$, together with the linking carbon atoms, forms a benzene ring, $R_4$ is additionally —($CH_2$)$_p$—$COR_9$ or —($CH_2$)$_q$OH, or, if $R_3$ and $R_5$ are hydrogen, $R_4$ is additionally a radical of formula II

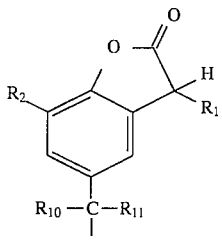
(II)

$R_8$ is hydrogen or $C_1$–$C_6$alkyl, $R_9$ is hydroxy, $C_1$–$C_{18}$alkoxy or

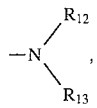

$R_{10}$ and $R_{11}$ are methyl groups or, together with the linking carbon atom, form a $C_5$–$C_8$-cycloalkylidene ring which is unsubstituted or substituted by 1 to 3 $C_1$–$C_4$alkyl groups;

$R_{12}$ and $R_{13}$ are each independently of the other hydrogen or $C_1$–$C_8$alkyl, and q is 2, 3, 4, 5 or 6.

10. A process according to claim 1, wherein at least two of the substituents $R_2$, $R_3$, $R_4$ and $R_5$ are hydrogen.

11. A process according to claim 1, wherein $R_3$ and $R_5$ are hydrogen.

12. A process according to claim 1, wherein $R_2$, $R_3$, $R_4$ and $R_5$ are each independently of one another hydrogen, chloro, hydroxy, $C_1$–$C_{18}$alkyl, $C_7$–$C_9$phenylalkyl, phenyl, $C_5$–$C_8$cycloalkyl, $C_1$–$C_6$alkoxy, cyclohexylcarbonyloxy or benzoyloxy, or each pair of substituents $R_2$ and $R_3$ or $R_3$ and $R_4$ or $R_4$ and $R_5$, together with the linking carbon atoms, forms a benzene ring, $R_4$ is additionally —($CH_2$)$_p$—$COR_9$, or if $R_3$ and $R_5$ are hydrogen, $R_4$ is additionally a radical of formula II $R_9$ is hydroxy or $C_1$–$C_{18}$alkoxy, and $R_{10}$ and $R_{11}$ are methyl groups or, together with the linking carbon atom, form a $C_5$–$C_8$-cycloalkylidene ring.

13. A process according to claim 1, wherein $R_2$ is $C_1$–$C_{18}$alkyl or cyclohexyl, $R_3$ is hydrogen, $R_4$ is $C_1$–$C_4$alkyl, cyclohexyl or a radical of formula II, $R_5$ is hydrogen, and $R_{10}$ and $R_{11}$ together with the linking carbon atom, form a cyclohexylidene ring.

14. A process according to claim 1, wherein $R'_{15}$ is hydrogen, $C_1$–$C_{18}$alkanoyl, $C_3$–$C_{18}$alkenoyl, $C_3$–$C_{18}$alkanoyl which is interrupted by oxygen, sulfur or >N—$R_8$; $C_6$–$C_9$cycloalkylcarbonyl, thenoyl, furoyl, benzoyl or $C_1$–$C_8$alkyl substituted benzoyl; naphthoyl or $C_1$–$C_{18}$alkyl-substituted naphthoyl; $C_1$–$C_{18}$alkanesulfonyl, fluoro-substituted $C_1$–$C_{18}$alkanesulfonyl; phenylsulfonyl or $C_1$–$C_8$alkyl-substituted phenylsulfonyl;

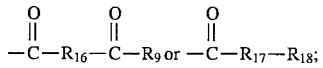

$R_{16}$ is a direct bond, $C_1$–$C_{12}$alkylene, $C_2$–$C_{12}$alkylene which is interrupted by oxygen, sulfur or >N—$R_8$; $C_2$–$C_{12}$alkenylene, $C_2$–$C_2$alkylidene, $C_7$–$C_{12}$phenylalkylidene, $C_5$–$C_8$cycloalkylene, $C_7$–$C_8$bicycloalkylene or phenylene, $R_{17}$ is oxygen or —NH—, and $R_{18}$ is $C_1$–$C_{12}$alkyl or phenyl.

15. A process according to claim 1, wherein $R_{15}$ is chloro, bromo or —$OR'_{15}$, $R'_{15}$ is hydrogen, $C_1$–$C_{12}$alkanoyl, $C_3$–$C_{12}$alkanoyl which is interrupted by oxygen; cyclohexylcarbonyl, benzoyl, naphthoyl, $C_1$–$C_{12}$alkanesulfonyl, fluoro-substituted $C_1$–$C_{12}$-alkanesulfonyl; phenylsulfonyl or $C_1$–$C_4$alkyl-substituted phenylsulfonyl; or

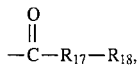

$R_{17}$ is —NH—, and $R_{18}$ is $C_1$–$C_8$alkyl or phenyl.

16. A process according to claim 1, wherein $R_{15}$ is —OR$'_{15}$,

R$'_{15}$ is hydrogen, $C_1$–$C_4$alkanoyl or

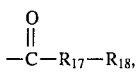

$R_{17}$ is —NH—, and $R_{18}$ is $C_1$–$C_4$alkyl.

17. A process according to claim 1, wherein the reaction is carried out in the presence of a catalyst.

18. A process according to claim 17, wherein the catalyst is selected from the group consisting of a protonic acid, a Lewis acid, an aluminium silicate, an ion exchange resin, a zeolite, a naturally occurring sheet silicate and a modified sheet silicate.

19. A process according to claim 17, wherein the catalyst is a naturally occurring sheet silicate or a modified sheet silicate.

20. A process according to claim 19, wherein the naturally occurring sheet silicate is a Fulcat or Fulmont type.

21. A process according to claim 1, wherein, when n is 1, the molar ratio of the compound of formula III to the compound of formula IV is 1:1 to 1:20 and, when n is 2, the molar ratio of the compound of formula III to the compound of formula IV is 3:1 to 2:1.

* * * * *